United States Patent
Qiang et al.

(10) Patent No.: US 9,926,573 B2
(45) Date of Patent: Mar. 27, 2018

(54) GLYPHOSATE-TOLERANT GENE AND USE THEREOF

(71) Applicant: NANJING AGRICULTURAL UNIVERSITY, Nanjing, Jiangsu (CN)

(72) Inventors: Sheng Qiang, Nanjing (CN); Chanjuan Mao, Nanjing (CN); Shiguo Chen, Nanjing (CN); Weimin Dai, Nanjing (CN); Xiaoling Song, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 72 days.

(21) Appl. No.: 15/109,580

(22) PCT Filed: Sep. 5, 2013

(86) PCT No.: PCT/CN2013/001039
§ 371 (c)(1),
(2) Date: Jul. 1, 2016

(87) PCT Pub. No.: WO2014/036806
PCT Pub. Date: Mar. 13, 2014

(65) Prior Publication Data
US 2016/0340689 A1    Nov. 24, 2016

(30) Foreign Application Priority Data

Sep. 6, 2012    (CN) .......................... 2012 1 0326805
Sep. 4, 2013    (CN) .......................... 2013 1 0396762

(51) Int. Cl.
    *C12N 15/82*    (2006.01)
    *C12Q 1/68*    (2006.01)
    *C07K 14/415*    (2006.01)
    *C12N 9/10*    (2006.01)

(52) U.S. Cl.
CPC ........ *C12N 15/8275* (2013.01); *C07K 14/415* (2013.01); *C12N 9/1092* (2013.01); *C12Q 1/6895* (2013.01); *C12N 2800/22* (2013.01); *C12Q 2600/13* (2013.01); *C12Q 2600/158* (2013.01)

(58) Field of Classification Search
None
See application file for complete search history.

(56) References Cited

FOREIGN PATENT DOCUMENTS

CN    101285057 A    10/2008
CN    102816777 A    12/2012

OTHER PUBLICATIONS

Mao et al, Planta, 2016, vol. 243, pp. 321-335.*
Alignments of SEQ ID Nos. 2, 4 and 6 with those of Mao et al, Planta, 2016, vol. 243, pp. 321-335.*
Dec. 12, 2013 Search Report issued in International Patent Application No. PCT/CN2013/001039.
Dec. 12, 2013 Written Opinion issued in International Patent Application No. PCT/CN2013/001039.
Mar. 10, 2015 International Preliminary Report on Patentability issued in International Patent Application No. PCT/CN2013/001039.
E. Kathleen Archer et al; "Current Views on Chloroplast Protein Import and Hypotheses on the Origin of the Transport Mechanism;" Journal of Bioenergetics and Biomembranes; 1990; vol. 22; No. 6; pp. 789-810.
Scott R. Baerson et al; "Glyphosate-Resistant Goosegrass. Identification of a Mutation in the Target Enzyme 5-Enolpyruvylshikimate-3-Phosphate Synthase;" Plant Physiology; Jul. 2002; vol. 129; pp. 1265-1275.
Lynda G. Blackburn et al; "Subtle Effects of Herbicide Use in the Context of Genetically Modified Crops: A Case Study with Glyphosate (Roundup®);" Ecotoxicology; 2003; vol. 12; pp. 271-285.
Wilbur H. Campbell et al; "Codon Usage in Higher Plants, Green Algae, and Cyanobacteria;" Plant Physiol.; 1990; vol. 92; pp. 1-11.
Marcio de Castro Silva Filho et al; "Mitochondrial and chloroplast targeting sequences in tandem modify protein import specificity in plant organelles;" Plant Molecular Biology; 1996; vol. 30; pp. 769-780.
M. Gallo-Meagher et al; "Herbicide Resistant Transgenic Sugarcane Plants Containing the bar Gene;" Crop Science.; 1996; vol. 36; pp. 1367-1374.
Fidel González-Torralva et al; "Target site mutation and reduced translocation are present in a glyphosate-resistant Lolium multiflorum Lam. biotype from Spain;" Plant Physiology and Biochemistry; 2012; vol. 58; pp. 16-22.
Marie Mannerlöf et al; "Transgenic sugar beet tolerant to glyphosate;" Euphytica; 1997; vol. 94; pp. 83-91.
Duncan J. Maskell et al; "Cloning and Nucleotide Sequence of the aroA Gene of *Bordetella pertussis*;" Journal of Bacteriology; Jun. 1998; vol. 170; No. 6; pp. 2467-2471.
C H NG et al; "Gene polymorphisms in glyphosate-resistant and—susceptible biotypes of Eleusine indica from Malaysia;" Weed Research; 2003; vol. 43; pp. 108-115.
Alejandro Peñaloza-Váquez et al; "Expression of the hygromycin B phosphotransferase gene confers tolerance to the herbicide glyphosate;" Plant Cell Reports; 1995; vol. 14; pp. 482-487.
Stephen B. Powles et al; "Evolution in Action: Plants Resistant to Herbicides;" Annual Review of Plant Biology; 2010; vol. 61; pp. 317-347.
Stephen B Powles; "Evolved glyphosate-resistant weeds around the world: lessons to be learnt;" Pest Management Science; 2008; vol. 64; pp. 360-365.

(Continued)

*Primary Examiner* — Eileen O Hara
(74) *Attorney, Agent, or Firm* — Oliff PLC

(57) ABSTRACT

Disclosed is a glyphosate-tolerant gene. The nucleotide sequence of the gene is SEQ ID NO: 1, SEQ ID NO: 3 or SEQ ID NO: 5, and a mutant form of the gene that maintains the glyphosate-tolerant activity. The amino acid sequence of a protein encoded by the gene is respectively SEQ ID NO: 2, SEQ ID NO: 4, or SEQ ID NO: 6, and a mutant form of amino acids in a conserved region 1 of positions 280 to 294 and in a conserved region 2 of positions 416 to 433. Also disclosed is the use of the gene and the mutant form thereof in the production of a glyphosate-resistant/tolerant plant.

5 Claims, No Drawings

(56) References Cited

OTHER PUBLICATIONS

Marulak Simarmata et al; "Inheritance of glyphosate resistance in rigid ryegrass (Lolium rigidum) from California;" Weed Science; 2005; vol. 53; pp. 615-619.
D. Sost et al; Abstract of "Substitution of Gly-96 to Ala in the 5-enolpyruvylshikimate-3-phosphate synthase of Klebsiella pneumoniae results in a greatly reduced affinity for the herbicide glyphosate;" Arch Biochem Biophysics; Nov. 1, 1990; vol. 282; No. 2; pp. 433-436.
A M Wakelin et al; "A target-site mutation is present in a glyphosate-resistant Lolium rigidum population;" European Weed Research Society; 2006; vol. 46; pp. 432-440.
Qin Yu et al; "Glyphosate, paraquat and ACCase multiple herbicide resistance evolved in a Lolium rigidum biotype;" Planta; 2007; vol. 225; pp. 499-513.
Ewa Zboinska et al; "Organophosphonate Utilization by the Wild-Type Strain of *Pseudomonas fluorescens*;" Applied and Environmental Microbiology; Sep. 1992; vol. 58; No. 9; pp. 2993-2999.
Zhang Meng et al; "Glyphosate-tolerant mechanisms in field bindweed Convolvulus arvensis;" Acta Phytophylacica Sinica; Dec. 2011; vol. 38; No. 6; pp. 551-556.
H. Zhou et al; Glyphosate-tolerant CP4 and GOX genes as a selectable marker in wheat transformation; Plant Cell Reports; 1995; vol. 15; pp. 159-163.
Stephen O Duke et al; "Mini-review Glyphosate: a once-in-a-century herbicide;" Pest Management Science; 2008; vol. 64; pp. 319-325.
Genbank ABE77393.4; EPSP synthase [Allium macrostemon]; Jan. 22, 2007.

\* cited by examiner

GLYPHOSATE-TOLERANT GENE AND USE THEREOF

BACKGROUND

Technical Field

The present invention relates to the field of plant molecular biology and plant genetic engineering. Specifically, the present invention relates to a glyphosate-resistant/tolerant gene of plant origin and a protein encoded thereby, to a method for obtaining a highly glyphosate-resistant gene mutant by genetic engineering by artificial mutation, and to a highly glyphosate-resistant/tolerant gene of plant origin obtained after artificial mutation. The gene is expressed in a plant by genetic transformation to allow the plant to be glyphosate-resistant, thereby selectively controlling the weed in the crop fields by using glyphosate. The present invention is also applicable to crop breeding, and screening of plant cell culture.

Related Art

Since the initial use of 2,4-D in 1946, chemical herbicides has had a history of over 60 years, and made an enormous contribution to the global food production and agricultural modernization (Powels and Yu, 2010). Among them, glyphosate (N-(phosphonomethyl)glycine) is the most important and widely used herbicide by far (Duke and Powles, 2008). Since its development in 1974 by the Monsanto Company, glyphosate quickly occupied a leading position in the world's herbicide market because of its broad spectrum, low toxicity, safety, no residue in soil and other characteristics. The mechanism of toxic action of glyphosate is mainly by competitively inhibiting EPSPase, that is, 5-enolpyruvyl-shikimate-3-phosphate synthase (EPSPS), which is widely present in fungi, bacteria, algae, and higher plants, but not in animals. Glyphosate is an analogue to and has a molecular formula closely similar to that of phosphoenolpyruvic acid (PEP). Glyphosate can compete with PEP for binding to the EPSPase to form a EPSPase • 3-shikimate-3-phosphate (S3P)• glyphosate complex, whereby the synthesis of EPSP and thus the synthesis of aromatic amino acids are blocked, leading to the death of plants. The non-selectivity in killing the crops and weeds limits the use of glyphosate in, and causes great loss to agricultural production. Glyphosate is widely used in the control of weeds in crop fields only after glyphosate-resistant transgenic crops (e.g. soybean, corn, cotton and rape) are developed and commercialized in 1996 (Powles, 2008). At present, glyphosate is the pesticide with the largest production that has a market share of nearly 20% in the global pesticide market, and has an annual sale of more than 2,000,000,000 $. New glyphosate-resistant crop varieties are cultivated by many researchers through various methods.

At present, it is the most effective means to obtain resistant crops by breeding glyphosate-resistant plants by genetic engineering. In the genetic engineering methodologies, a resistant EPSPase encoding gene of bacterial origin is generally utilized, the product of which cannot be competitively inhibited by glyphosate due to a decreased binding activity, thus ensuring the normal synthesis of aromatic amino acids in plants. The commonly used resistant genes may be derived from *Salmonella typhimurium, Agrobacierium tumefaciens, Escherichia coli, Pseudomonas*, and so on. Transgenic plants expressing bacterial EPSPase and exhibiting glyphosate resistance are obtained by many researches through genetic engineering methodologies using the resistant genes (Sust and Amrherin, 1990; Blackburn and Boutin, 2003; Maskell, 1998; Gallo and Irvine, 1996; Zhou et al., 1995; Mannerlof et al., 1997; Penaloza et al., 1995; Zboinskaetal., 1992). Among them, glyphosate-resistant transgenic soybean is massively planted in the United States, Brazil and other countries. However, as food or a food material, the safety of the crops with the resistant genes of bacterial origin is persistently a focus of argument.

It is also found in plants that mutation of a single amino acid site in EPSPase results in the resistance to glyphosate. *Eleusine indica* has an 8 to 12 fold increased resistance to glyphosate, due to the mutation of proline at position 106 in EPSPS to serine or threonine (Pro106Ser/Thr) (Baerson et al., 2002; Ng et al., 2003). Different varieties of glyphosate-resistant *Lolium rigidum* have 2 different mutations of proline at position 106 in EPSPS, that is, substitution with threonine or alanine (Pro106Thr/Ala) (Wakelin and Preson, 2006; Yu et al., 2007). Mutation of the amino acid at position 182 in EPSPase from proline (P) to serine (S) is one of the mechanisms underlying the glyphosate resistance in *Lolium multiflorum* (Gonzalez-Torralva, 2012). The affinity to glyphosate is reduced through gene mutations at these effective sites, thereby enhancing the resistance of the weeds to glyphosate.

Furthermore, it is confirmed through studies on glyphosate-resistant EPSPS genes in weeds that the resistance of weeds to glyphosate is largely caused by the change in polarity resulting from amino acid mutations. The non-polar proline at position 106 in EPSPS encoding gene in glyphosate-resistant *Eleusine indica* and *Lolium rigidum* is mutated respectively to polar serine and threonine (Baerson, 2002; Wakelin and Preston, 2006). The amino acids at position 101 in EPSPS gene of glyphosate-resistant *Lolium rigidum* and *Convolvulus arvensis* L are mutated respectively from non-polar proline and non-polar phenylalanine to polar serine (Simarmata and Penner, 2008; Zhang et al., 2011). The change in the polarity of amino acids may affect the affinity of EPSPase to glyphosate.

A patent is filed for the glyphosate-resistant EPSPS gene of *Eleusine indica* by the Monsanto Company. However, to improve the resistance level of transgenic crops and increase the diversity of resistant genes, there is still a need in production applications for new glyphosate-resistant/tolerant genes and glyphosate-resistant/tolerant plants based thereon. Compared with the glyphosate-resistant genes of bacterial origin and other heterogeneous genes from other categories, the ecological environmental and food safety risks of the glyphosate-resistant/tolerant crops bred with the evolutionary or natural resistant gene of plant original are lower, whereby the public acceptance is improved.

SUMMARY

To solve the defects existing in the prior art, an objective of the present invention is to provide a new glyphosate resistant/tolerant gene obtained by preliminary screening of a large number of plants for resistance to glyphosate based on the natural tolerance of plants in the nature, a series of gene mutants modified therefrom, and use of the genes in the production of glyphosate-resistant transgenic plants and as a screening marker in cultivation of plant cells.

To achieve the above objective, the present invention provides three glyphosate-tolerant genes (LS-EPSPS) LsEPSPS1, LsEPSPS2, and LsEPSPS3 having a nucleotide sequence of SEQ ID NO: 1, SEQ ID NO: 3, and SEQ ID NO: 5 respectively.

The present invention further provides a glyphosate-resistant/tolerant protein/polypeptide, which has an amino acid sequence of SEQ ID NO: 2, SEQ ID NO: 4, or SEQ ID NO: 6, or has an amino acid sequence that is no less than 84% identical to the above amino acid sequences.

SEQ ID NO: 2, SEQ ID NO: 4, and SEQ ID NO: 6 represent the amino acid sequences encoded by SEQ ID NO: 1, SEQ ID NO: 3, and SEQ ID NO: 5 respectively. All the three amino acid sequences comprise four specific sites, which are 144m, 184i, 232a, and 273m in *Ophiopogon japonicus*, and are 146m, 186i, 234a and 275m in *Liriope spicata* and *Liriope platyphylla*, and correspond to positions 70, 107, 153, and 192 of the amino acid sequence of the EPSPase in *E. Coli*.

The protein/polypeptides represented by the amino acid sequences of SEQ ID NO: 2, SEQ ID NO: 4, and SEQ ID NO: 6 consist of a signal peptide and a mature protein.

The present invention further provides a method for obtaining a mutant gene by mutation that maintains the glyphosate-tolerant activity, which comprises the steps of:

(1) obtaining a mutant gene, where the amino acid sequence (SEQ ID NO: 7, which is an amino acid sequence of SEQ ID NO: 4 removed of the signal peptide) of a protein encoded by the mutant gene has at least one amino acid mutation in the amino acid sequences of positions 280 to 294 (a conserved region 1) and positions 416 to 433 (a conserved region 2) of SEQ ID NO: 7; and (2) screening the mutant gene with glyphosate, to obtain a highly glyphosate-resistant mutant gene.

The mutant gene is obtained by error prone PCR, site directed mutagenesis, artificial synthesis, or other gene mutation technologies.

By the above method, the present invention provides a glyphosate-tolerant gene, where the amino acid sequence of a protein encoded by the gene has at least one amino acid mutation in both a conserved region 1 of positions 280 to 294 and a conserved region 2 of positions 416 to 433 of SEQ ID NO:7. Particularly, one or more mutations at the following sites are introduced to the conserved region 1 and the conserved region 2: conserved region 1: 1) lysine at position 284; 2) phenylalanine at position 285; and 3) leucine at position 289; and conserved region 2: 1) valine at position 4161 2) arginine at position 421;3) aspartate at position 422;4) glycine at position 424; and 5) cysteine at position 425.

The present invention also provides a glyphosate-resistant mutant gene, where the protein encoded by the gene has at least one amino acid mutation both in a conserved region 1 and in a conserved region 2. The amino acid mutation in the conserved region 1 is 1) the mutation of the amino acid at position 284 from lysine to arginine; 2) the mutation of the amino acid at position 285 from phenylalanine to tyrosine; and 3) the mutation of the amino acid at position 289 from leucine to histidine. The amino acid mutation in the conserved region 2 is 1) the mutation of the amino acid at position 416 from valine to glutamate; 2) the mutation of the amino acid at position 421 from arginine to glycine; 3) the mutation of the amino acid at position 422 from aspartate to valine; 4) the mutation of the amino acid at position 424 from glycine to cysteine; and 5) the mutation of the amino acid at position 425 from cysteine to tyrosine.

The present invention further provides a glyphosate-tolerant protein, where the amino acid sequence from positions 280 to 294 of the protein is any one of SEQ ID NOs: 8-14, and the amino acid sequence from positions 416 to 433 of the protein is any one of SEQ ID NOs: 15-28.

The present invention further provides a glyphosate-tolerant protein, which has an amino acid sequence of any one of SEQ ID NOs: 29-52.

The present invention further provides a gene having a nucleotide sequence encoding the protein/polypeptide above.

One or more variations may be artificially introduced to the nucleic acid sequence of the glyphosate-tolerant gene, and then the variant molecules are screened with glyphosate, to obtain a variant molecule that maintains the glyphosate-resistant/tolerant activity. For example, many variant LSEPSPS molecules may be produced through low fidelity PCR, and then screened with glyphosate, to obtain a variant molecule that has the glyphosate-resistant/tolerant activity maintained or enhanced. The glyphosate-resistant/tolerant LS-EPSPS genes LsEPSPS1, LsEPSPS2, and LsEPSPS3, and a mutant gene LSE-EPSPS obtained therefrom that maintain the resistance to glyphosate are collectively referred to as glyphosate resistant/tolerant genes (LSEPSPSs).

The present invention further provides an antibody able to bind to the protein/polypeptide.

A signal peptide sequence may be designed and artificially added to the amino acid sequence encoded by the gene of the present invention, to facilitate the expression in plants.

By using the amino acid sequence encoded by the gene of the present invention, a nucleic acid sequence may be designed and artificially synthesized to have codon optimized for facilitating the expression in plants, as described in for example, Campbell and Gowri (1990) (Plant Physiology, 92: 1-11). The present invention further provides an expression vector comprising the glyphosate resistant/tolerant gene, which is a prokaryotic expression vector or a plasmid for plant transformation.

Where a prokaryotic expression vector comprising expression elements is constructed, the expression elements include a promoter and the glyphosate resistant/tolerant gene, and the vector plasmid may be the PET series, pMAL-p2X or pRSET-A, and others. In the prokaryotic expression vector, the promoter may be T7 phage promoter or strong promoters such as lac (lactose promoter), trp (tryptophan promoter), PL and PR (promoter left and promoter right of λ phage), and tac (hybrid promoter of lactose and tryptophan).

When a plasmid for plant transformation comprising expression elements is further constructed with the glyphosate resistant/tolerant gene, the expression elements comprise a promoter, the glyphosate resistant/tolerant gene bearing a chloroplast signal peptide, and a terminator. When a monocotyledon is transformed, the promoter may be a maize ubiquitn promoter, a rice actin promoter, or other promoters. The terminator may be a terminator derived from *Agrobacterium tumefaciens* or other terminators. A DNA fragment encoding the signal peptide that is expressed in the same reading frame is connected to the 5' terminus of the glyphosate-resistant/tolerant LSE-EPSPS gene, and the signal peptide may direct the LSEPSPS protein to enter the chloroplast. The signal peptide may be a Rubisco sub-unit signal peptide (de castro Silva Filho 1996 Plant Mol. Biol. 30: 767-780), a plant EPSPS signal peptide (Archer 1990 J. Bioenerg. Biomemb. 22(b): 789-810), or other signal peptides that enables the EPSPS to function, or no signal peptide is present. The expression element may be integrated into the genome of plants by transformation with *Agrobacterium* (strain LAB4404), and stably inherited and expressed.

The present invention further provides a plant cells comprising the glyphosate resistant/tolerant gene, and a glyphosate-resistant/tolerant plant comprising the plant cell.

The present invention further provides use of the glyphosate resistant/tolerant gene in the production of a glyphosate-resistant/tolerant plant, and as a transgene screening marker for plants.

In the production of a glyphosate-resistant/tolerant plant with the glyphosate resistant/tolerant gene, a plasmid for plant transformation containing the LSEPSPS expression element is used. The methods and steps for plant transformation may vary from species to species of plant, and may be slightly different for different varieties of the same species. The technologies and methods for plant transformation are well known and mature in the art. The glyphosate resistant/tolerant gene is generally introduced to an immature embryo, mature embryo, immature callus or protoplast of a plant by a gene gun or through *agrobacterium* mediated transformation. Then, the plant cells containing the gene are screened in different concentrations of glyphosate containing medium. The plant cells are differentiated to obtain a transformed shoot, which is cultivated in a rooting medium to obtain a plant seedling for planting. Alternatively, the glyphosate resistant/tolerant gene is introduced to the pollen of the plant through *agrobacterium* mediated transformation or a pollen mediated method, to obtain transgenic seeds. Further, glyphosate may be sprayed onto the transformed seedling and progenies thereof, to screen out and remove the untransformed plant and progenies that lose the LSEPSPS gene. Specifically, the plant may be produced through the steps of:

(1) constructing a plasmid for plant transformation containing the glyphosate resistant/tolerant gene by using a recombinant DNA technique;

(2) transferring the plasmid for plant transformation constructed in the step (1) to a plant tissue by a gene gun or through *agrobacterium* mediated transformation or a pollen mediated method, and screening the plant cells containing the gene in a glyphosate containing medium; and (3) differentiating the plant cells screened in the step (2), to obtain a transformed shoot, which is cultivated in a rooting medium to obtain a plant seedling, thereby obtaining the glyphosate-resistant/tolerant plant.

The plant may be rice, corn, cotton, wheat, soybean, potato, sweet potato, cereal, sorghum, barley, rapeseed, sugar cane, tobacco, lawn grass (*Cynodon dactylon, Zoysia japonica*, ryegrass, bluegrass, *Vicia Gigantea Bunge*, bentgrass, seashore *paspalum*) or pasture plants (alfalfa, red clover, and *Paspalum vaginatum*), vegetables (*Brassica chinensis*, Chinese cabbage, cucumber, celery, pepper, and eggplant), and flowers (e.g. *Rosa chinensis*, carnation, and chrysanthemum).

When the glyphosate resistant/tolerant gene is used as a transgene screening marker for plants, LSEPSPS are caused to express in plant cells by known molecular cloning technologies. Generally, an expression element expressed in plant is constructed, which comprises a promoter, the LSEPSPS bearing a chloroplast signal peptide, and a terminator. The expression element may be cloned as a screening marker into a plasmid for plant transformation. The plasmid for plant transformation generally further contains the target gene and other DNA sequence. The plasmid for plant transformation may be introduced to a plant tissue by a gene gun or through *agrobacterium* mediated transformation or a pollen mediated method, and a medium containing a suitable concentration of glyphosate may selectively kill the plant cells without the plasmid DNA introduced, thereby screening out the plant cells containing the target LSEPSPS gene.

The present invention is applicable to all the plants, including monocotyledonous plants and dicotyledonous plants.

Compared with the prior art, the present invention has the following benefits. In the present invention, in place of screening the resistant biotypes of plants or microorganisms grown in a glyphosate environment for a long period of time, the resistance to glyphosate of *Ophiopogon japonicas* of Liliaceae is discovered by preliminary intense screening of a large number of plants for resistance to glyphosate based on the natural tolerance of plants in the nature, and a much higher glyphosate resistance is achieved by genetic engineering by error prone PCR, thereby providing a new option for cultivating glyphosate-resistant/tolerant crops, increasing the versatility of the glyphosate-resistant/tolerant transgenic technologies, and thus decreasing the ecological risk of the herbicide-resistant/tolerant transgenic technologies. Furthermore, compared with heterogeneous genes from different categories, the ecological environmental and food safety risks of the glyphosate-resistant/tolerant crops cultivated with the gene of the present invention are lower because the gene is of plant origin, whereby the public acceptance is improved.

DETAILED DESCRIPTION

The present invention is described in detail below with reference to specific examples.

EXAMPLE 1

Glyphosate Resistance Test of *Ophiopogon japonicus, Liriope spicata*, and *Liriope platyphylla*

*Ophiopogon japonicus, Liriope spicata*, and *Liriope platyphylla* with even growth vigor were sprayed with glyphosate at a concentration of 0, 375, 750, 1500, 3000, 6000, 12000, and 24000 ai·g/ha. The test plant materials were treated according to the designed dosage, with four replicates per treatment. After spray, the plants were observed for the degree of damage. The injury level was surveyed and recorded weekly, an inhibition curve was plotted, and the logistic regression analysis was conducted to calculate the ED50 value. The test was triplicated. The results show that the glyphosate resistance of *Ophiopogon japonicus, Liriope spicata*, and *Liriope platyphylla* was 4.73, 5.06, and 5.8 times of that of an ordinary plant respectively.

EXAMPLE 2

Cloning of EPSPS Gene

A RT-PCR procedure was performed with a reverse transcription product of the total RNA of *Ophiopogon japonicus, Liriope spicata*, and *Liriope platyphylla* as a template, and using a primer designed with a conserved sequence of the EPSPS gene. The amplified fragment was cloned into a pMD19-T vector, for sequencing and alignment by BLAST.

After the sequence of the conserved region was obtained, full-length cloning of the EPSPase gene was performed by the RACE (rapid-amplification of cDNA ends) technology. The RNA of *Ophiopogon japonicus, Liriope spicata*, and *Liriope platyphylla* was reversely transcribed by using the adaptor primer AP. A gene specific primer was designed by using the obtained sequence of the conserved region of the gene, and used together with a primer specific for the 3'-terminus in the RT-PCR.

Based on the obtained target gene fragment, the 5' terminus was cloned by the terminal deoxynucleotidyl transferase (TDT) method. After the gene specific primer was designed and used in reverse transcription, the amplification with a single primer was carried out, and then the amplified product was purified. The purified amplified product was tailed by dCTP and TdT, the product with a dC tail was amplified by PCR using an anchor primer, and finally the preliminary PCR product was amplified again by nested PCR. The amplified sequence was cloned and sequenced.

Finally, the conserved region, the 3'-terminal sequence, and the 5'-terminal sequence were ligated, to obtain the full-length cDNA sequence of the EPSPS gene of *Ophiopogon japonicas*. The EPSPS gene of *Ophiopogon japonicas* has a nucleotide sequence of SEQ ID NO: 1, and is designated as LsEPSPS 1, which encodes the protein having an amino acid sequence of SEQ ID NO: 2. The EPSPS gene of *Liriope spicata* has a nucleotide sequence of SEQ ID NO: 3, and is designated as LsEPSPS 2, which encodes the protein having an amino acid sequence of SEQ ID NO: 4. The EPSPS gene of *Liriope platyphylla* has a nucleotide sequence of SEQ ID NO: 5, and is designated as LsEPSPS 3, which encodes the protein having an amino acid sequence of SEQ ID NO: 6.

EXAMPLE 3

Analysis and Alignment of Amino Acid Sequences Encoded by the EPSPS Gene in *Ophiopogon japonicus, Liriope Spicata*, and *Liriope platyphylla*

About 260 amino acid sequences of EPSPase that are highly identical to the EPSPase of *Ophiopogon japonicus, Liriope spicata*, and *Liriope platyphylla* were analyzed and compared by the MAGA software. It was found that compared with other plants, the amino acid sequence of the EPSPase of *Ophiopogon japonicus, Liriope spicata*, and *Liriope platyphylla* has 4 specific amino acids, that is, 144m, 184i, 232a, and 273m (the sequencing numbering is based on the amino acid sequence (SEQ ID NO: 2) of the EPSPase of *Ophiopogon japonicas*, which correspond to positions 70, 107, 153, and 192 of the amino acid sequence of the EPSPase in E. Coli, and are 146m, 186i, 234a and 275m in *Liriope spicata* and *Liriope platyphylla*). The amino acids at these sites are conserved in *Ophiopogon japonicus, Liriope spicata*, and *Liriope platyphylla*, but are absent in other plants. The presence of these amino acids results in the tolerance of *Ophiopogon japonicus, Liriope spicata*, and *Liriope platyphylla* to glyphosate.

The Met at positions 144 and 273 contains a methylthio (—SCH3) group, and other amino acids do not. The presence of the methylthio group may possibly cause the structure of EPSPase to change.

The Ile at position 184 has one more —CH2- in the R group than Val and Thr in other plants. The increase of —CH2- may possibly cause the spatial volume at the same site to increase, such that the steric hindrance existing upon binding to glyphosate is increased.

The Ala at position 232 has two less —CH3 than Val in other plants, such that the length of the R group and the steric hindrance are decreased, possibly causing the structure of the EPSPase to change.

The amino acid sequence (having 516 amino acids in total) of the EPSPase of *Ophiopogon japonicas* was predicted for secondary structure, and compared with a known map of the backbone of the EPSPase. It was found that there are a total of 12 helices in all the amino acid sites (except for the signal peptide), the methionine at position 144 is located at the turn from the $2^{nd}$ to the $3^{rd}$ helix in about a third region; the isoleucine at position 484 is located at the $3^{rd}$ helix; the alanine at position 232 is located at the $2^{nd}$ sheet of the $4^{th}$ and $5^{th}$ helix; and the methionine at position 273 is located at the sheet of the $5^{th}$ and $6^{th}$ helix.

The 144Met is close to the glyphosate binding site 22Lys and the S3P binding sites 23Ser and 27Arg. The 184Ile and the glyphosate binding sites 96Gly and 94Asn are all located at the $3^{rd}$ helix, and the increased backbone length may possibly cause the steric hindrance existing upon binding to glyphosate to increase, thereby reducing the affinity of glyphosate to the EPSPase. The 232Ala is intimately close to 124Arg. The 273Met and its spatial conformation may have impact on the 169Ser, 170Ser, 171Gln and 197Ser that are located in the $5^{th}$ domain. The four sites are in a region relevant to the binding of a substrate to the enzyme, and the change of the four amino acids may cause the structure of the EPSPase to change, such that the binding of the EPSPase to the substrate is changed, leading to the glyphosate resistance.

EXAMPLE 4

Mutagenesis by Error Prone PCR

A primer was designed according to the known EPSPS gene of *Liriope spicata*, and mutagenesis by error prone PCR was carried out by using the gene as a template. The system had a total reaction volume of 100 μl containing 10 μl of 10×PCR buffer for mutagenesis, 10 μl of 10×dNTP mixture, 10 μl of each of the primer pair, 10 μl of MnCl2, 10 μl of template, 1 μl of TaqDNA polymerase, 39 μl of ultrapure water. The mixed reaction system was fed to an eppendorf tube in a volume of 10 μl for cyclic PCR reactions, including denaturization at 94° C. for 5 min, denaturization at 94° C. for 1 min, annealing at 50° C. for 1 min, extension at 72° C. for 1 min, and extension at 72° C. for 10 min. After 30 cycles, the product was subjected to electrophoresis on a 110% agarose gel and ethidium bromide (EB) staining, and then detected through UV analysis. The PCR product on the agarose gel was recovered by using a DNA purification kit available from Promega Corporation. A target fragment of about 1300 bp was obtained after amplification.

EXAMPLE 5

Construction of Recombinant Plasmid and Screening and Identification of Positive Clone The pQE80L plasmid vector and the product from PCR mutagenesis were cleaved respectively with SphI and HindIII restriction enzyme, to obtain gene fragments having a viscous terminus (and having a size of about 4.7 kb and 1.3 kb respectively). The enzymatically cleaved gene fragments were ligated by a $T_4$ ligase, and used for transformation of competent *E. coli* cells. Colonies able to grow on a medium containing 100 mmol/L of glyphosate were picked up for extracting plasmid. The *E. coli* cells were further transformed with the plasmid, such that the *E. coli* cells previously unable to grow on the medium containing 100 mmol/L of glyphosate acquired the glyphosate resistance. The nucleotide sequence was sequenced to be SEQ ID NOs: 29-52.

EXAMPLE 6

Assay of Mutation Sites in Amino Acid Sequence of Highly Glyphosate-Resistant LSE-EPSPS The clone able to normally grow on the medium containing 100 mmol/L of glyphosate might comprise a mutant that has a much higher glyphosate-resistant activity than the original LS-EPSPS gene. Therefore, the nucleotide sequence in the mutation region of the glyphosate- resistant clone obtained in Example 2 was determined. The result shows that mutations exist in the conserved region 1 (of amino acids 280 to 294) and 2 (of amino acids 416 to 433).

TABLE 1

Mutations in the conversed region of the amino acid sequence of EPSPase

| Conversed region | Sequence | Mutation |
|---|---|---|
| Residues 280-294 of SEQ ID NO: 7 | $^{280}$QGDVKFAEVLEKMG$^{294}$A | K284R, F285Y, L289H |
| Residues 416-433 of SEQ ID NO: 7 | $^{416}$VPVTIRDPGCTRKTFPD$^{433}$Y | V416E, R421G, D422V, G424C, C425Y |

EXAMPLE 7

Confirmation of the Functions of the Amino Acid Mutations in the Conserved Region To confirm whether the mutation sites in the conserved region of amino acids 280-294 and 416-433 leads to the glyphosate resistance, a series of mutant genes were obtained through site-directed mutation in the present invention, and transferred to E. Coli cells. The cells were cultured on a medium containing 100 mmol/L of glyphosate at 37° C. for 48 hrs, and observed for the growth. The clones with mutant genes and able to normally grow were statistically analyzed. The result shows that the amino acid sequence of positions 280 to 294 of the glyphosate-resistant protein is any one of SEQ ID NOs: 8-14, and the amino acid sequence of positions 416 to 433 is any one of SEQ ID NOs: 15-28. The proteins satisfying the above conditions have the glyphosate resistance.

EXAMPLE 8

Expression of LS-EPSPS and LSE-EPSPS Gene in E. Coli

The LS-EPSPS gene was cloned into the vector PET-28a, and transferred to E. Coli BL21 (DE3), to obtain a transgenic strain. The reading frame of the transgenic strain was expressed under control of the T7 promoter in the PET system.

The stain transformed with LS-EPSPS-PET or PET-28a (empty vector, control) was incubated in LB, and grown in an LB liquid medium containing Kan at 37° C. when $OD_{600}$ reached 0.6, until the OD value reached about 0.4. The culture was inoculated in an amount of 1% into an LB liquid medium containing Kan in which the glyphosate concentration was 0, 1500, 3000, 4500, 6000, 7500, 9000, 10500 and 12000 mg/L respectively, and IPTG was added to a final concentration of 1 mmol/L. After 12-16 hrs, the OD value was measured. In this way, the growth curve of the transgenic strain and the strain with empty PET-28a vector at different glyphosate concentrations were obtained, and the logistic regression analysis was conducted. The test result shows that at 7500 and 9000 mg/L of glyphosate, the OD % (percentages of the OD value relative to the control) of the stain transformed with LS-EPSPS-PET is about 70% and 60%, and the OD % of the strain transformed with PET-28a is only 20% and 1% of the control, suggesting that the glyphosate resistance of the LS-EPSPS transgenic strain is greatly higher than that of the strain with the empty vector at 7500 and 9000 mg/L of glyphosate. According to the logistic regression equation, the $ED_{50}$ value of the LS-EPSPS transgenic strain is also greatly higher than that of the strain with the empty vector PET-28a. These indicate that the LS-EPSPS gene has glyphosate-resistant/tolerant activity.

The pET-28a plasmid vector and the product LSE-EPSPS gene from PCR mutagenesis were cleaved respectively with EcoRI and HindIII restriction enzyme, to obtain gene fragments having a viscous terminus (and having a size of about 5.8 kb and 1.3 kb respectively). The enzymatically cleaved gene fragments were ligated by a $T_4$ ligase, and used for transformation of competent BL21 (DE3) cells, to obtain a recombinant strain. The reading frame of the recombinant strain was expressed under control of the T7 promoter in the PET system. The transformants BL21(LSE-EPSPS) and BL21(LS-EPSPS) were respectively incubated in 5 ml of a LB liquid medium containing 50 µg/ml of Kan at 200 rpm in an air bath at 37° C., until the cell density reached $10^8$ cells/ml. The culture was inoculated in an amount of 1% into a fresh LB liquid medium containing 50 µg/ml of Kan and incubated at 200 rpm and 37° C. until $OD_{600}$=0.75. At this time, IPTG was added to a final concentration of 1 mmol/L, to induce the synthesis of recombinant protein. The cells were cultured for another 3 hrs under the above conditions. The cells were collected by centrifugation. Following the method as described by Laemmli, the cells were re-suspended in a SDS-PAGE sample loading buffer, and then the protein was separated by SDS-PAGE gel electrophoresis. After electrophoresis, the protein was stained with 20% Coomassie brilliant blue.

EXAMPLE 9

Preparation of Crude EPSPase Extract

BL21(LSE-EPSPS), and BL21(LS-EPSPS) were respectively transformed by incubating with 5 ml of an LB liquid medium containing 50 µg/ml of Kan, and grown at 200 rpm in an air bath at 37° C., until the cell density reached $10^8$/ml. The culture was inoculated in an amount of 1% into a fresh LB liquid medium containing 50 µg/ml of Kan and incubated at 200 rpm and 37° C. until $OD_{600}$=0.75. At this time, IPTG was added to a final concentration of 1 mM, to induce the synthesis of recombinant protein. The cells were cultured for another 3 hrs under the above conditions. The cells were collected by centrifugation, re-suspended in a buffer A (50 mM Tris-Cl, 0.1 mM DTT, pH 7.2), frozen at −70° C., and then thawed at room temperature. Subsequently, the cell suspension was homogenized by using a homogenizer available from Fluko Corp, and then centrifuged at 12000 rpm for 30 min. The cell debris was discarded. The resulting supernatant was the crude EPSPase extract, and could be used in the determination of various indices of the enzyme.

EXAMPLE 10

Ex-vivo EPSPase Activity Assay 0.5 g of the seedlings of *Ophiopogon japonicus, Liriope spicata, Liriope platyphylla* and wide-type *Arabidopsis thaliana* were weighed, added with 150 ml of an extraction buffer A [containing 100 mmol/L Tris pH 7.5, 1 mmol/L EDTA, 10% (V/V) glycerol, 1 mg/L BSA, 10 mmol/L Vitamin C (Vc), 1 mmol/L benzamidine, 5 mmol/L DTT, and 20 mg/ml PVPP], ground and homogenized, filtered through 6 layers of gauze, and centrifuged at 12000 rpm and 4° C. The resulting supernatant was the crude EPSPase extract, 40 µl of an enzymatic reaction system (containing 50 mmoL/L HEPES pH 7.5, 1 mmol/L $(NH_4)_6Mo_7O_{24}$, 1 mmol/L PEP, 2 mmol/L S3P, 1 mg/L BSA, and glyphosate in a concentration of 0, 100, 200, 500, 800, 1000 and 2000 µmol/L) was preheated at 25° C. for 5 min, then added with 10 µl of the enzyme extract, enzymatically reacted at 25° C. for 15 min, placed in boiling water rapidly to quench the enzymatic reaction, and then cooled to room temperature. Following the method as described by Lanzetta and Alvarez (1979), the reaction was developed for 30 min by adding 800 µl of malachite green hydrochloride, and then 100 µl of a 34% sodium citrate solution was added. After 30 min, the OD660 value was determined at 660 nm on a spectrophotometer. The results show that the EPSPase activity of the wide-type *Arabidopsis thaliana* declines obviously when the glyphosate concentration is 500 µmol/L, while the EPSPase activity of *Ophiopogon japonicas, Liriope spicata* and *liriope platyphylla* declines obviously only when the glyphosate concentration reaches 800 µmol/L, 1000 µmol/L, and 1000 µmol/L respectively. Logistic regression analysis was performed and the $ED_{50}$ was calculated. The $ED_{50}$ values for the EPSPase activity of *Arabidopsis thaliana, Ophiopogon japonicas, Liriope spicata* and *Liriope platyphylla* were 560, 860, 1090, and 1070 µmol/L. It can be seen that the EPSPase activity of *Ophiopogon japonicas, Liriope spicata* and *Liriope platyphylla* was obviously higher than that of wide-type *Arabidopsis thaliana*.

EXAMPLE 11

Construction of Eukaryotic Expression Vector

Generally, a plant expression vector containing 35S promoter is suitable for the transfer of a foreign gene to a dicotyledonous plant due to the high promoter efficiency and the easy transcription and expression in transgenic progenies. However, the 35S promoter is unsuitable for use in a monocotyledonous plant. The monocotyledonous transgenic plant mainly uses the actin, emu, and ubquitin promoters, which are derived from monocotyledonous plants, and suitable for the transfer of a foreign gene to a monocotyledonous plant. The commonly used terminator is nopaline synthase (NOS) terminator, and the marker gene may be neomycin phosphotransferase II (npt II) gene, chloramphenicol acetyl transferase (cat) gene, luciferase (LUC) gene, green fluorescent protein (GFP) gene or beta-glucosidase (Gus) gene, etc. For example, the plant expression vector pBI121-LSEPSPS was constructed by recombinant DNA technologies, in which the LSEPSPS gene was cloned into the plant expression vector PBI121, and then it was confirmed by enzymatic cleavage and electrophoresis that the LSEPSPS gene was successfully inserted into the plant expression vector PBI121. Subsequently, the recombinant plasmid pBI121-LSEPSPS was transferred into the *Agrobacterium tumefaciens* strain EHA105 by the freeze-thaw method. A Kan plate was used for screening the positive clone, the grown individual colonies were identified by PCR, and the recombinant plasmid was confirmed to be transferred to the *Agrobacterium lumefaciens* strain EHA105. Different expression vectors might be selected for different plants, or the expression vector might be reconstructed and modified, for example, the promoter, terminator or marker gene may be replaced or increased.

EXAMPLE 12

Resistance Identification of Transgenic *Arabidopsis thaliana*

The wide-type *Arabidopsis thaliana* was transformed by the floral dip method. The PBI121-LSEPSPS plant expression vectors were constructed with the LS-EPSPS gene, artificially synthesized similar sequence LSE-EPSPS, and variant LSE-EPSPS gene obtained through low fidelity PCR amplification, and transferred to the *Agrobacterium tumefaciens* strain EHA105 by the freeze-thaw method. 10 ml of a suspension of *Agrobacterium tumefaciens* cells transformed with a corresponding plasmid was prepared. 1 day before transformation, the cell suspension was transferred to a large bottle and incubated overnight, and the $OD_{600}$ was in the range of 1.2 to 1.6 on the second day when the cell suspension was removed for use. The cell suspension was centrifuged at room temperature at 5000 r/m for 15 min and the supernatant was discarded. Then, the cell pellet was suspended in a corresponding volume of a permeating medium, such that the $OD_{600}$ was about 0.8. The cell suspension of *Agrobacterium tumefaciens* was injected to a mist sprayer, and sprayed onto the above-ground plant parts, until there were water drops falling from the plants. The plants (plants of generation T0) were covered with a preservative film for moisture reservation, and then cultivated in an incubation chamber. After 2 to 3 days, the preservative film was removed. The plants could be watered about 1 week after transformation. The plants were continuously cultivated until mature. The seeds (generation T1) were collected, placed in a dry environment for about 1 week, and then screened for transformant. The successfully transformed plants were identified to be glyphosate resistant, and might be used as a transgene screening marker.

The transgenic *Arabidopsis thaliana* plant was obtained by screening. The stem of the tissue cultured seedling of the non-transgenic and the LS-EPSPS transgenic *Arabidopsis thaliana* was used as an explant for callus induction in an MS medium containing 2.0 mg/L of 6-BA and 0.1 mg/L of NAA. After 2-3 weeks of growth, the callus was treated with glyphosate. The transgenic resistant callus passing the Kan resistance screening and the wide-type callus were inoculated into an MS medium containing 0 mg/L, 50 mg/L, 100 mg/L, 200 mg/L, 400 mg/L, 600 mg/L, 800 mg/L, and 1000 mg/L of glyphosate respectively, and then cultured at 25° C. in alternative light/dark 16 h/8 h. The results were statistically calculated after two weeks. The callus of the control *Arabidopsis thaliana* becomes yellow and gradually mortifies when the glyphosate concentration is 50 mg L. In contrast, the callus of the transgenic *Arabidopsis thaliana* can still normally grow when the glyphosate concentration reaches 600 mg/L, and is inhibited in growth and becomes brown and yellow only when the glyphosate concentration reaches 800 mg/L.

EXAMPLE 13

Production of Glyphosate-resistant/Tolerant Transgenic Rape

At present, the commonly used transgenic methods mainly include *agrobacterium* mediated transformation, laser microbeam puncture, PEG mediated transformation, electroporation, microinjection and pollen mediated method. The production of glyphosate-resistant/tolerant transgenic rape was described with pollen mediated method as an example.

After the rape entered the blossom period, 10 to 15 of buds that were on a main stem or on a first order branching of the main stem and would be in blossom in 1 to 2 days were manually emasculated, and enclosed with a bag after others buds on the stem or branching were removed. Meanwhile, the inflorescence of the same variety that would be in blossom in the second day was enclosed with a bag, for pollen removal in the second day. In the morning of the second day, 0.4 g of the pollen was removed from the flower on the plant that was in blossom on that day and enclosed with a bag, suspended in 25 ml of a 7.5% sucrose solution, and ultrasonicated for the $1^{st}$ time. Then 20 µg of a plasmid DNA containing the EPSPS gene was added to the solution and ultrasonicated for the $2^{nd}$ time. After the second treatment, 10 µL of 1/10000 (W/V) boric acid was added to the solution, and the stigmas of the rape emasculated one day before was pollinated with the treated pollen, enclosed with a bag and labeled. The number of pollinated buds was recorded. The bag was removed 5 to 6 days after pollination, to allow the pollinated plants to develop fully. Finally, the seeds were harvested.

EXAMPLE 14

Production of Glyphosate-resistant/Tolerant Transgenic Corn

The receptor material was sowed in a greenhouse at an interval of 7 days. The corn material was pollinated under control, as desired by the test. 10-13 days after pollination, the embryo of corn was used as a recipient for transformation. After the corncob was antisepticized with sodium hypochlorite, the embryo was peeled out carefully without damaging the embryo, and then washed 4 times with a dip solution (containing AS). Then, a concentration of *Agrobacterium* cell suspension was added and stood for 10 to 30 min. The embryo was then removed, aspirated off by sterilized filter paper, transferred to a culture medium for coincubation, and then coincubated for 2 to 5 days at 25° C. (in the dark). Subsequently, the embryo was transferred to a quiescent medium, and incubated for 7 days at 28° C. in the dark. During the dip and coincubation process, the cell concentration was such that OD500=0.3 to 0.5, the dip time was 10 min, and the coincubation time was 3 days. The embryo was transferred from the quiescent medium to a resistance screening medium containing glyphosate, and incubated in the dark. The embryo was initially incubated for 14 days under a low selection stress of 10 mg/L herbicide, then under a high selection stress of 80 mg/L herbicide, and finally under at an increased screening concentration of 160 mg/L. The callus appeared to be brown and water soaking was eliminated during each sub-culture, and the normally grown callus was broken by a forceps, and subjected to selective culture separately. During the subculture and screening process, the embryo was frequently observed, the material that was found to be contaminated or have reoccurrence of *Agrobacterium* was removed immediately, and the non-contaminated material was continuously cultured. Furthermore, the browning tissue mass was often excluded, or the non-contaminated tissue mass was transferred to a fresh medium of the same ingredients. After the tissue mass was enlarged, the large mass was often made small, and subcultured and screened for consecutive 3 times. The selected resistant callus was then transferred to a regenerative medium I, and recovered and cultured for 15 days or more (in the dark). The resistant callus was then transferred to a regenerative medium II and cultured for germination at 28° C. under irradiation with light of 3000 1× for 12 hrs a day. After the regenerated corn plant was grown to have 3 leaves, the seedling was transplanted to a bottle containing a rooting medium and cultured indoor. After the seedling had a large root, the seedling was removed from the bottle, flushed off the medium with water, and grown in a small pot filled with nutritive soil and vermiculite (1:3). When the corn plant was grown to have additional 2 to 3 leaves, the plant was grown in the field or in a big pot and after further three to four leaves emerged, DNA was extracted from the leaves for detection by PCR. It was confirmed that the leaves contain the transferred LSEPSPS gene.

EXAMPLE 15

Production of Glyphosate-resistant/Tolerant Transgenic Cotton

The plant expression vector plasmid DNA was extracted in a large amount. The buds that were in blossom in the next day were self crossed. Because the cotton was frequently out crossed and the natural out crossing rate was about 10%, the foreign pollen generally caused the intervariety hybridization. One day before blossom, the corolla elongated rapidly, the yellow or cream white corolla was protruded from the bud just like a finger, and the bud would be in blossom in the next. Such buds were selected, and bound tightly with a thread at the front end of the finger-like corolla, while the other end of the thread was tied to the boll stem, as a marker upon harvest. About 20-24 hrs after blossom (that is, the next day), the young ovary from desirable fruiting branch and floret position was selected as the object for transformation. Generally, the flowers at the first and second fruit setting node of each fruiting branch were used for transgenic operations. The cotton bolls on these fruit setting node generally had a high boll formation rate, which facilitate the harvest of more seeds. A 50 µl microsampler was used as the tool for microinjection. Before and after use, the microsampler was washed with a diluent detergent, and then rinsed with distilled water. Upon injection, the petal was removed or peeled off, and the style was smoothed. When the petal was peeled off, caution should be taken to avoid the damage to the epidermal layer of the young ovary, so as to avoid the increase in exfoliation rate. A microinjector was held by the right hand, the young ovary removed of the petal was gently supported with the left hand, and the needle was moved from the smoothed style to about two thirds of the ovary length along the longitudinal direction of the ovary, and then withdrawn to about one third of the ovary length.

After harvest, the cotton seeds (generation T0) obtained through transformation by a pollen tube pathway mediated method were used for cultivation of seedlings in pots at room temperature, and the cotton leaves were sprayed with an aqueous glyphosate amine salt solution (at an application rate of 1000 g/ha based on glyphosate) in the 2-3 leaf stage. The plants were observed for the growth after 1 week, and the plants having chlorosis spots on the surface of the leaves were eradicated. To obtain highly glyphosate-resistant transgenic cotton plants, 3 consecutive rounds of screening were carried out at an interval of 10-14 days. The normally grown plants were considered as the plants having the resistant gene. A total of 3 plants were obtained.

EXAMPLE 16

Production of Transgenic Glyphosate-resistant/Tolerant Tabacum

*Agrobacterium* activation—Coincubation: the dipped leaves were placed on a tabacum shoot differentiation medium (MS+IAA 0.5 mg/L+6-BA 2 mg/L) on which 2 layers of filter paper were laid, and incubated for 4 days at 25° C. in the dark. Screening of resistant shoot: the co-incubated tabacum explants were transferred to a resistant shoot screening medium (MS+IAA 0.5 mg/L+6-BA 2 mg/L+Kan 100 mg/L+Carb 500 mg/L), and sprouted after 2-3 weeks. Rooting: after the resistant shoot was grown to about 1 cm, the resistant shoot was transferred to a rooting medium (MS+Kan 100 mg/L+Carb 500 mg/L), and after 1-2 weeks, an adventitious root was formed. The antiseptic tabacum seeding was planted in greenhouse, and applied with 1%, 2%, 3%, 4%, 5%, and 6% of lyphosate (trade name Roundup) respectively when 6-8 true leaves were formed. The incubation was continued for another two weeks and the resistance of the tabacum to glyphosate was observed. Yellowing occurred to the leaves of the sensitive plants, and the resistant plants grew normally. A total of 5 plants were obtained.

EXAMPLE 17

Production of Transgenic Glyphosate-resistant/Tolerant Cucumber

Culture of bacterial strain: individual colony of *Agrobacterium tumefaciens* containing the constructed plant expression vector was picked up from a plate, inoculated in 5 ml of a culture medium (LB+50 mg/L kanamycin (Kan)), cultured for 16 hrs at 28° C. and 200 r/min, then inoculated in 90 ml of a fresh culture medium (LB+50 mg/L kanamycin), cultured at the same conditions to the exponential growth phase (4-5 hrs, OD≅0.8-1.2), washed 3 times with liquid MS, re-suspended in an MS liquid medium such that the OD value was 0.2-0.3, and then used for transformation. Callus induction and plant regeneration: the cucumber seeds were immersed in 75% ethanol and treated for 30 s, then treated with a calcium hypochlorite solution for 15 min, washed 5 times with sterilized water, sowed on a germination medium, and germinated at 25° C. in the dark. After 2-3 days of germination, the cucumber cotyledon was cut into squares of 5 mm, and dipped with *Agrobacterium tumefaciens* cells (containing the LSEPSPS gene) in exponential growth phase properly diluted in the MS medium for a period of time. The dipped explants were placed on a regeneration medium, incubated for 2 days at 24-25° C. in the dark, transferred to a germination induction medium containing carbenicillin and a concentration of glyphosate, and incubated for 2-3 weeks at 24-25° C. in the dark for callus differentiation. The resistant shoot obtained from the callus produced from the cotyledon was transferred to a 1/2 MS medium (containing carbenicillin and a concentration of glyphosate) to obtain a transformed plant.

EXAMPLE 18

Production of Transgenic Glyphosate-resistant/Tolerant China Rose

The mature leaflet explants of China rose were inoculated onto a callus induction medium containing 0.5 mg/L 2,4-D and 3.0 mg/L pCAP with the leaf back facing downward, and incubated for 20 days under light irradiation. The fresh callus subcultured for 20-30 days was dipped in an *Agrobacterium* cell suspension (OD600=0.8) for 20 min, then the callus was poured, air dried in sterile filter paper, inoculated in a co-culture medium containing 100 µM AS and improved 1/2 MS salt, co-cultured at 25° C. in the dark, and co-incubated with an EHA105 dipped culture for 3-4 days, until the *Agrobacterium* cells about the callus were preferably grown into a visible colony. After co-incubation, the callus was washed 1-2 times with sterile water, air dried in sterile filter paper, inoculated in a selection medium containing 70 mg/L hygromycin and 300 mg/L cephamycin, selectively cultured at 25° C. in the dark, and sub-cultured once every 2-3 weeks, for screening and proliferation of resistant callus. The GUS reaction detection was performed on the resistant callus after 3 months of selection, different portions of a mass of resistant callus appeared dark blue, light blue, or no blue reaction, indicating obvious chimera. It was found through PCR detection that a target fragment might be amplified from the resistant callus. The resistant callus was propagated, and then induction and detection of regenerated plants were carried out.

EXAMPLE 19

Production of Transgenic Glyphosate-resistant/Tolerant *Cynodon dactylon*

The stipes of *Cynodon dactylon* had a high meristematic activity. A stem section with about 0.5-1.0 cm of stipe was used as an explant. The surface of the stem section was cleaned with tapped water, soaked in 70% alcohol, washed 3 times with sterile water, antisepticised for 10 min with 0.1% mercury chloride, and then washed 3 times with sterile water. Water on the surface of the stem section was aspirated off by sterile filter paper, and then the stem section was inoculated in an induction medium. The callus was induced in an MS medium containing 2 mg/L 2,4-D+3 mg/L NAA+ 0.2 mg/L 6-BA, which was subcultured for 2 weeks, and then transferred to a MS differentiation medium containing 3 mg/L 6-BA+4.0 mg/L KT. The callus was differentiated in an artificial climatic chamber at 28° C. under 16 h-irradiation with light of 10-30 uEm-2s-1, and subcultured once in the same medium every 2 weeks. The differentiated small plant was inoculated in an MS rooting medium containing 0.3 mg/L NAA, transferred to a hormone-free 1/2 MS medium for sound seedling after 2 weeks of rooting culture, and then planted. The callus was soaked in an *Agrobacterium* cell suspension with an OD600 value of about 0.5 at 25° C. for 10 min, and the surplus cell suspension was aspirated off with sterile filter paper. The callus was placed in an MS induction medium, co-cultured for 2 days in the dark, and then washed with sterilized water containing 500 mg/L Carb. 50 mg/L hygromycin was used as the substance for screening. After 3 rounds of screening, the regenerated seedling was about 15 cm long, transferred to a greenhouse at this time, and hardened for 2 weeks. The survived seedling was subjected to GUS histochemical staining and PCR identification, to obtain a positive plant which was planted in a greenhouse and naturally grew.

EXAMPLE 20

Preparation of Anti-LSEPSPS Monoclonal Antibody

A recombinant monoclonal expression colony containing the LSEPSPS gene were placed in an LB medium (containing 50 mg/L Kan), and incubated at 37° C. and 300 rpm, until the cells are grown to the late exponential growth phase. IPTG was added at a final concentration of 0.025 mmol/L, and the expression was induced for 8 hrs at a low temperature of 22° C. The cells were collected by centrifugation at 10000 rpm for 10 min. A protein loading buffer was added, boiled for 5 min, and identified on 12% SDS-PAGE, such that the gene was efficiently expressed in E. Coli BL21 (DE3). The prepared bacterial cells were homogenized by ultrasonization, and centrifuged for 20 min at 4° C. and 12000 rpm. The supernatant was collected, and purified by affinity chromatography. The Balb/c mice were immunized by using the purified recombinant EPSPS antigen. The mouse spleen B lymphocytes were fused to the mouse myeloma cells SP2/0 in the presence of polyethylene glycol (PEG), and the monoclonal hybridoma cell line that stably excreted anti-LSEPSPS antibody was screened by ELISA. The hybridoma cell line was injected into the abdominal cavity of the mice, and the produced ascitic fluid contained high-titer monoclonal antibody. The IgG in the ascitic fluid was purified by using saturated ammonium sulfate.

EXAMPLE 21

Identification of Glyphosate Resistance of LSEPSPS Molecules Originated from Variation or Protein Expression Variant LSEPSPS molecules that maintained the glyphosate-resistant activity might be obtained by artificially introducing a single or a plurality of variations to LSEPSPS. For example, numerous variant LSEPSPS molecules might be produced by low fidelity PCR, from which variant LSEPSPS molecules that also maintained the glyphosate-resistant activity might be obtained by screening with glyphosate. The codon degeneracy existed, that is, except for methionine and tryptophan, every amino acid had at least two codons. As such, the amino acid sequence would not have incorrect amino acids resulting from unexpected replacement of a certain base to some extent. By deducing the base sequence encoded by the amino acid sequence obtained from the translation of the LSEPSPS gene, multiple sequences similar to LSEPSPS might be obtained, which also had glyphosate resistance. PBI121-LSEPSPS plant expression vectors were constructed with artificially synthesized sequences similar to LSEPSPS and variant LSEPSPS gene obtained by low fidelity PCR amplification, and transferred into the Agrobacterium tumefaciens strain EHA105 by the freeze-thaw method. 10 ml of a suspension of Agrobacterium tumefaciens cells transformed with a corresponding plasmid was prepared. 1 day before transformation, the cell suspension was transferred to a large bottle and incubated overnight, and the $OD_{600}$ was in the range of 1.2 to 1.6 on the second day when the cell suspension was removed for use. The cell suspension was centrifuged at room temperature at 5000 r/m for 15 min and the supernatant was discarded. Then, the cell pellet was suspended in a corresponding volume of a permeating medium, such that the $OD_{600}$ was about 0.8. The cell suspension of Agrobacterium tumefaciens was injected to a mist sprayer, and sprayed onto the above-ground plant parts, until there were water drops falling from the plants. The plants (plants of generation $T_0$) were covered with a preservative film for moisture reservation, and then cultivated in an incubation chamber. After 2 to 3 days, the preservative film was removed. The plants could be watered about 1 week after transformation. The plants were continuously cultivated until mature. The seeds (generation $T_1$) were collected, placed in a dry environment for about 1 week, and then screened for transformant. The successfully transformed plants were identified to be glyphosate resistant, and might be used as a transgene screening marker.

Apparently, the present invention is not limited to the above examples, and many variations may be made thereto. All the variations may be directly derived by or suggested to those of ordinary skill in the art based off the present disclosure, which fall within the protection scope of the present invention.

What is claimed is:

1. A glyphosate-tolerant protein, wherein the conserved region 1 of positions 280 to 294 in the amino acid sequence of the protein is any one of SEQ ID NOs: 8-14, the conserved region 2 of positions 416 to 433 is any one of SEQ ID NOs: 15-28, and the remainder is the same as that in the amino acid sequence of SEQ ID NO: 7; or the amino acid sequence of the protein is any one of SEQ ID NOs: 29-52.

2. A glyphosate-tolerant gene having a nucleotide sequence encoding the protein according to claim 1.

3. A glyphosate-resistant/tolerant plant comprising the gene according to claim 2.

4. A method for producing the glyphosate-resistant/tolerant plant according to claim 3, comprising:
   (1) constructing a plasmid for plant transformation containing the gene by using a recombinant DNA technique;
   (2) transferring the plasmid for plant transformation constructed in the step (1) to a plant tissue by a gene gun or through agrobacterium mediated transformation or a pollen mediated method, and screening plant cells containing the glyphosate resistant/tolerant gene in a glyphosate containing medium; and
   (3) differentiating the plant cells screened in the step (2), to obtain a transformed shoot, which is cultivated in a rooting medium to obtain a plant seedling, thereby obtaining the glyphosate-resistant/tolerant plant.

5. A glyphosate-resistant/tolerant plant produced by introducing a plasmid for plant transformation containing the gene according to claim 2 into plant tissue, screening for plant cells containing the gene, and differentiating and cultivating the screened plant cells.

* * * * *

SEQUENCE LISTING

```
<160> NUMBER OF SEQ ID NOS: 52

<210> SEQ ID NO 1
<211> LENGTH: 1551
<212> TYPE: DNA
<213> ORGANISM: Ophiopogon japonicus

<400> SEQUENCE: 1
atggagcaag cgatcatggc tcagggcgtc gccaccaacc tcggcctctc tacttcctcc      60
cttcggaatc cgaagctcat cgcggcctct tctccttctt cttcgattcg gatcggatcg     120
gggctgaaac tagggttttc ggttggcttg aaggggggagg ttgggaggag gagggcggtt     180
agggtttcgg cgtcggtggc ggcggcggag aagccgtcga cggtgccgga gatcgtgctg     240
cagccgatca aggagatctc cgggacgatc aagctcccgg gatccaagtc gttgtccaat     300
```

```
cggattctgc ttcttgccgc gctcgctgag ggaactactg ttgtggacaa tttgttggac      360
agtgatgaca ttagctatat gcttgctgca cttaaaacac ttgggctctc tgtagaagac      420
gatagtgtca tgaaacgtgc aactgttgtg ggatctggag gtcaatttcc tgttgggaaa      480
gattccaaag aggtccaact ttttctagga aatgcaggga ctgcaatgcg tcctctgaca      540
gctgctgtta ttgctgctgg tggaaatgca agttacatac ttgatggggt accacgaatg      600
agggagagac ctataggga cttggttgtt ggtttgaagc agttgggtgc agatgttgat      660
tgcattttgg gaactgactg tccacctgtt cgtgccaatg caaatggagg tcttccaggg      720
ggaaaggtta aactctctgg atcaattagc agtcagtatt tgactgcgtt gcttatggct      780
gcgcccttag ctcttggaga tgtggagatt gagatcatgg ataaacttat ttcagtccca      840
tatgttgaaa tgacgcttaa actgatgaaa cgttttggag tcagtgtgga gcattccagt      900
agctgggata ggttcttcat caagggcggc caaaagtaca gtcccctgg aaatgcttat       960 gtggaaggtg atgcttcgag cgctagttat tttctcgcag gcgcagcagt caccggcggc     1020
acggtaactg ttgagggttg tggcacaagc agtttgcagg gtgatgtaaa attcgctgaa     1080
gttcttgaga aaatgggggc aaaggttaca tggacagaga atagcgtcac agtaacaggc     1140
ccgccgcaag atccttccaa gaagaagcga ttgcaagcca ttgatgtcaa tatgaataaa     1200
atgcctgatg ttgccatgac tctagctgtt gttgctcttt atgctgatgg tccgactgcc     1260
attagagacg ttgcttcatg gcgagtaaag gagactgaac gaatgattgc tatctgtaca     1320
gagcttagaa agctgggagc aacggtggaa gaaggacccg attactgcgt gatcaccccg     1380
cccgagaagt tgaacgtggc agcaatcgac acctacgacg atcacaggat ggccatggcg     1440
ttctctcttg cagcctgtgc ggatgcaccc gtcacgatca gagacccgg ctgcacccgc      1500 aaaactttcc cggactattt tgaggtattg cagaggtttg cgaagcacta a              1551

<210> SEQ ID NO 2
<211> LENGTH: 516
<212> TYPE: PRT
<213> ORGANISM: Ophiopogon japonicus
<220> FEATURE:
<221> NAME/KEY: SIGNAL
<222> LOCATION: (1)..(63)
<220> FEATURE:
<221> NAME/KEY: CHAIN
<222> LOCATION: (64)..(516)
<220> FEATURE:
<221> NAME/KEY: ACT_SITE
<222> LOCATION: (144)..(184)
<223> OTHER INFORMATION: Met, Ile, Ala, Met

<400> SEQUENCE: 2

Met Glu Gln Ala Ile Met Ala Gln Gly Val Ala Thr Asn Leu Gly Leu
1               5                   10                  15

Ser Thr Ser Ser Leu Arg Asn Pro Lys Leu Ile Ala Ala Ser Ser Pro
            20                  25                  30

Ser Ser Ser Ile Arg Ile Gly Ser Gly Leu Lys Leu Gly Phe Ser Val
        35                  40                  45

Gly Leu Lys Gly Glu Val Gly Arg Arg Arg Ala Val Arg Val Ser Ala
    50                  55                  60

Ser Val Ala Ala Ala Glu Lys Pro Ser Thr Val Pro Glu Ile Val Leu
65                  70                  75                  80

Gln Pro Ile Lys Glu Ile Ser Gly Thr Ile Lys Leu Pro Gly Ser Lys
                85                  90                  95

Ser Leu Ser Asn Arg Ile Leu Leu Leu Ala Ala Leu Ala Glu Gly Thr
```

```
                100             105                 110
Thr Val Val Asp Asn Leu Leu Asp Ser Asp Ile Ser Tyr Met Leu
            115                 120             125
Ala Ala Leu Lys Thr Leu Gly Leu Ser Val Glu Asp Ser Val Met
        130                 135             140
Lys Arg Ala Thr Val Val Gly Ser Gly Gly Gln Phe Pro Val Gly Lys
145                 150                 155                 160
Asp Ser Lys Glu Val Gln Leu Phe Leu Gly Asn Ala Gly Thr Ala Met
                165                 170                 175
Arg Pro Leu Thr Ala Ala Val Ile Ala Ala Gly Gly Asn Ala Ser Tyr
            180                 185                 190
Ile Leu Asp Gly Val Pro Arg Met Arg Glu Arg Pro Ile Gly Asp Leu
        195                 200                 205
Val Val Gly Leu Lys Gln Leu Gly Ala Asp Val Asp Cys Ile Leu Gly
        210                 215                 220
Thr Asp Cys Pro Pro Val Arg Ala Asn Ala Asn Gly Gly Leu Pro Gly
225                 230                 235                 240
Gly Lys Val Lys Leu Ser Gly Ser Ile Ser Ser Gln Tyr Leu Thr Ala
                245                 250                 255
Leu Leu Met Ala Ala Pro Leu Ala Leu Gly Asp Val Glu Ile Glu Ile
            260                 265                 270
Met Asp Lys Leu Ile Ser Val Pro Tyr Val Glu Met Thr Leu Lys Leu
        275                 280                 285
Met Glu Arg Phe Gly Val Ser Val Glu His Ser Ser Ser Trp Asp Arg
        290                 295                 300
Phe Phe Ile Lys Gly Gly Gln Lys Tyr Lys Ser Pro Gly Asn Ala Tyr
305                 310                 315                 320
Val Glu Gly Asp Ala Ser Ser Ala Ser Tyr Phe Leu Ala Gly Ala Ala
                325                 330                 335
Val Thr Gly Gly Thr Val Thr Val Glu Gly Cys Gly Thr Ser Ser Leu
            340                 345                 350
Gln Gly Asp Val Lys Phe Ala Glu Val Leu Glu Lys Met Gly Ala Lys
        355                 360                 365
Val Thr Trp Thr Glu Asn Ser Val Thr Val Thr Gly Pro Pro Gln Asp
        370                 375                 380
Pro Ser Lys Lys Lys Arg Leu Gln Ala Ile Asp Val Asn Met Asn Lys
385                 390                 395                 400
Met Pro Asp Val Ala Met Thr Leu Ala Val Val Ala Leu Tyr Ala Asp
                405                 410                 415
Gly Pro Thr Ala Ile Arg Asp Val Ala Ser Trp Arg Val Lys Glu Thr
            420                 425                 430
Glu Arg Met Ile Ala Ile Cys Thr Glu Leu Arg Lys Leu Gly Ala Thr
        435                 440                 445
Val Glu Glu Gly Pro Asp Tyr Cys Val Ile Thr Pro Pro Glu Lys Leu
        450                 455                 460
Asn Val Ala Ala Ile Asp Thr Tyr Asp Asp His Arg Met Ala Met Ala
465                 470                 475                 480
Phe Ser Leu Ala Ala Cys Ala Asp Ala Pro Val Thr Ile Arg Asp Pro
                485                 490                 495
Gly Cys Thr Arg Lys Thr Phe Pro Asp Tyr Phe Glu Val Leu Gln Arg
            500                 505                 510
Phe Ala Lys His
        515
```

<210> SEQ ID NO 3
<211> LENGTH: 1557
<212> TYPE: DNA
<213> ORGANISM: Liriopes spicata

<400> SEQUENCE: 3

| | | | | | | |
|---|---|---|---|---|---|---|
| atggagcaag | cgatcatggc | taagggcgtc | gccaccaacc | tcggcctctc | cacttcctcc | 60 |
| cttgggaatc | cgaagctcat | cgtggcttct | tcttctcctc | ctccttcttc | gattcggatc | 120 |
| ggatcggggc | tgaaactagg | gttttcggtt | ggtttgaagg | ggggagttgg | gatgaggagg | 180 |
| gcggttacgg | tttcggcgtc | ggtggcggcg | gcggagaaac | cgtcgacggt | gccggagatc | 240 |
| gtgctgcagc | cgatcaagga | gatctcgggg | acgatcaagc | tcccgggatc | caagtcgttg | 300 |
| tccaatcgga | ttctgcttct | tgccgcgctc | gctgagggaa | ctactgttgt | ggacaattta | 360 |
| ttggacagtg | atgacattcg | ctatatgctt | gctgcactta | aaacgcttgg | gctcactgta | 420 |
| gaagacgata | gtgtcatgaa | acgtgcaact | gttgtgggat | ctggtggtca | atttcctgtt | 480 |
| gggaaagatt | ccaaagaggt | tcaacttttt | ctaggaaatg | cagggactgc | aatgcgtcct | 540 |
| ctgacagctg | ctgttattgc | tgctggtgga | aatgcaagtt | acatacttga | tggggtacca | 600 |
| cgaatgaggg | agaggcctat | aggggacttg | gttgttggct | tgaagcagtt | aggtgcagat | 660 |
| gttgattgca | ttttgggaac | tgactgtcct | cctgttcgtg | ccaatgcaca | tggaggtctt | 720 |
| ccaggaggaa | aggtgaaact | ctctggatca | attagcagtc | agtatttgac | tgcgttgctt | 780 |
| atggcagcgc | cctagctct | tggagacgtg | gagattgaga | tcatggataa | acttatttca | 840 |
| gtcccatatg | ttgaaatgac | gcttaaactg | atggaacgtt | ttggggttag | tgtggagcat | 900 |
| tccagtagct | gggataggtt | cttcatcaag | ggtggtcaaa | agtacaagtc | cctggaaat | 960 |
| gcttatgtgg | aaggtgatgc | ttcgagcgct | agttattttc | tcgcaggtgc | agcggtcact | 1020 |
| ggcggcacgg | taactgttga | gggttgtggc | acgagcagtt | tgcagggaga | tgtaaaattc | 1080 |
| gctgaagttc | ttgagaaaat | gggggcaaag | gttacatgga | cagagaatag | cgtcacagta | 1140 |
| acaggcccac | cgcaagatcc | ttccaagaag | aagcgattgc | gagccgttga | tgtcaatatg | 1200 |
| aataaaatgc | ctgatgttgc | catgactcta | gctgttgttg | ctctttatgc | tgatggtccg | 1260 |
| actgccatta | gagacgttgc | ttcttggcga | gtaaaggaga | ctgaacgaat | gattgctatt | 1320 |
| tgtacagaac | ttagaaagct | gggagcaaca | gtggaggaag | acccgatta | ctgcgtgatc | 1380 |
| accccaccgg | agaagctgaa | cgcgaatgca | atcgacacct | acgacgatca | caggatggct | 1440 |
| atggcgttct | ctctcgcagc | ctgtgcggat | gtacccgtca | cgatcagaga | ccccggttgc | 1500 |
| acccgcaaaa | ctttccccga | ctattttgag | gtattgcaga | ggttcacaac | gcactaa | 1557 |

<210> SEQ ID NO 4
<211> LENGTH: 518
<212> TYPE: PRT
<213> ORGANISM: Liriopes Spicatae
<220> FEATURE:
<221> NAME/KEY: SIGNAL
<222> LOCATION: (1)..(65)
<220> FEATURE:
<221> NAME/KEY: CHAIN
<222> LOCATION: (66)..(518)
<220> FEATURE:
<221> NAME/KEY: ACT_SITE
<222> LOCATION: (146)..(186)
<223> OTHER INFORMATION: Met, Ile, Ala, Met

<400> SEQUENCE: 4

-continued

```
Met Glu Gln Ala Ile Met Ala Lys Gly Val Ala Thr Asn Leu Gly Leu
1               5                   10                  15

Ser Thr Ser Ser Leu Gly Asn Pro Lys Leu Ile Val Ala Ser Ser Ser
            20                  25                  30

Pro Pro Pro Ser Ser Ile Arg Ile Gly Ser Gly Leu Lys Leu Gly Phe
            35                  40                  45

Ser Val Gly Leu Lys Gly Gly Val Gly Met Arg Arg Ala Val Thr Val
50                  55                  60

Ser Ala Ser Val Ala Ala Glu Lys Pro Ser Thr Val Pro Glu Ile
65                  70                  75                  80

Val Leu Gln Pro Ile Lys Glu Ile Ser Gly Thr Ile Lys Leu Pro Gly
                85                  90                  95

Ser Lys Ser Leu Ser Asn Arg Ile Leu Leu Ala Ala Leu Ala Glu
            100                 105                 110

Gly Thr Thr Val Val Asp Asn Leu Leu Asp Ser Asp Ile Arg Tyr
            115                 120                 125

Met Leu Ala Ala Leu Lys Thr Leu Gly Leu Thr Val Glu Asp Asp Ser
130                 135                 140

Val Met Lys Arg Ala Thr Val Val Gly Ser Gly Gln Phe Pro Val
145                 150                 155                 160

Gly Lys Asp Ser Lys Glu Val Gln Leu Phe Leu Gly Asn Ala Gly Thr
                165                 170                 175

Ala Met Arg Pro Leu Thr Ala Ala Val Ile Ala Ala Gly Asn Ala
            180                 185                 190

Ser Tyr Ile Leu Asp Gly Val Pro Arg Met Arg Glu Arg Pro Ile Gly
    195                 200                 205

Asp Leu Val Val Gly Leu Lys Gln Leu Gly Ala Asp Val Asp Cys Ile
    210                 215                 220

Leu Gly Thr Asp Cys Pro Pro Val Arg Ala Asn Ala His Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
            260                 265                 270

Glu Ile Met Asp Lys Leu Ile Ser Val Pro Tyr Val Glu Met Thr Leu
    275                 280                 285

Lys Leu Met Glu Arg Phe Gly Val Ser Val Glu His Ser Ser Ser Trp
    290                 295                 300

Asp Arg Phe Phe Ile Lys Gly Gln Lys Tyr Lys Ser Pro Gly Asn
305                 310                 315                 320

Ala Tyr Val Glu Gly Asp Ala Ser Ser Ala Ser Tyr Phe Leu Ala Gly
                325                 330                 335

Ala Ala Val Thr Gly Gly Thr Val Thr Val Glu Gly Cys Gly Thr Ser
            340                 345                 350

Ser Leu Gln Gly Asp Val Lys Phe Ala Glu Val Leu Glu Lys Met Gly
            355                 360                 365

Ala Lys Val Thr Trp Thr Glu Asn Ser Val Thr Val Thr Gly Pro Pro
370                 375                 380

Gln Asp Pro Ser Lys Lys Lys Arg Leu Arg Ala Val Asp Val Asn Met
385                 390                 395                 400

Asn Lys Met Pro Asp Val Ala Met Thr Leu Ala Val Val Ala Leu Tyr
            405                 410                 415

Ala Asp Gly Pro Thr Ala Ile Arg Asp Val Ala Ser Trp Arg Val Lys
```

```
                420               425              430
Glu Thr Glu Arg Met Ile Ala Ile Cys Thr Glu Leu Arg Lys Leu Gly
            435                 440                 445

Ala Thr Val Glu Glu Gly Pro Asp Tyr Cys Val Ile Thr Pro Pro Glu
        450                 455                 460

Lys Leu Asn Ala Asn Ala Ile Asp Thr Tyr Asp Asp His Arg Met Ala
465                 470                 475                 480

Met Ala Phe Ser Leu Ala Ala Cys Ala Asp Val Pro Val Thr Ile Arg
                485                 490                 495

Asp Pro Gly Cys Thr Arg Lys Thr Phe Pro Asp Tyr Phe Glu Val Leu
            500                 505                 510

Gln Arg Phe Thr Thr His
        515
```

<210> SEQ ID NO 5
<211> LENGTH: 1557
<212> TYPE: DNA
<213> ORGANISM: Liriope platyphylla

<400> SEQUENCE: 5

| | | | | | |
|---|---|---|---|---|---|
| atggagcaag | cgatcatggc | taaggggggtc | gccaccaacc | tcagcctctc | cacttcctcc | 60 |
| cttgggaatc | cgaagctcat | cgtggcctct | tcttctcctc | cttcttcttc | gattcggatc | 120 |
| ggatcggggc | tgaaactagg | gttttcggtt | ggtttgaagg | ggggagttgg | gatgaggagg | 180 |
| gcggttacgg | tttcggcgtc | ggtggcggcg | gcggagaagc | cgtcgacggt | gccggagatc | 240 |
| gtgctgcagc | cgatcaagga | gatctcgggg | acgatcaagc | tcccgggatc | caagtcgttg | 300 |
| tccaatcgga | ttctgcttct | tgccgcgctc | gctgagggaa | ctactgttgt | ggacaatttg | 360 |
| ttggacagtg | atgacattcg | ctatatgctt | gctgcactta | aaacgcttgg | gctcgctgta | 420 |
| gaagatgata | gtgtcatgaa | acgtgcaact | gttgtgggat | ctggtggtca | atttcctgtt | 480 |
| gggaaagatt | ccaaagaggt | tcaacttttt | ctaggaaatg | cagggactgc | aatgcgtcct | 540 |
| ctgacagctg | ctgttattgc | tgctggtgga | aatgcaagtt | acatacttga | tggggtacca | 600 |
| cgaatgaggg | agaggcctat | aggggacttg | gttgttggct | tgaagcagtt | aggtgcagat | 660 |
| gttgattgca | ttttgggatc | tgactgtcct | cctgttcgtg | ccaatgcaca | tggaggtctt | 720 |
| ccaggaggaa | aggtgaaact | ctctggatca | attagcagtc | agtatttgac | tgcgttgctt | 780 |
| atggcagcgc | ccttagctct | tggagatgtg | agattgaga | tcatggataa | acttatttca | 840 |
| gtcccatatg | ttgaaatgac | gcttaaactg | atggaacgtt | ttggtgttag | tgtggagcat | 900 |
| tccagtagct | gggataggtt | cttcatcaag | ggtggtcaaa | agtacaagtc | ccctggaaat | 960 |
| gcttatgtgg | aaggtgatgc | ttcgagcgct | agttattttc | tcgcaggtgc | agcggtcact | 1020 |
| ggcggcacgg | taactgttga | gggttgtggc | acgagcagtt | tgcagggaga | tgtaaaattc | 1080 |
| gctgaagttc | ttgagaaaat | gggggcaaag | gttacatgga | cagagaatag | cgtcacagta | 1140 |
| acaggcccac | cgcaagatcc | ttccaagaag | aagcgattgc | gagccattga | tgtcaatatg | 1200 |
| aataaaatgc | tgatgttgc | catgactcta | gctgttgttg | ctctttatgc | tgatggtccg | 1260 |
| actgccatta | gagacgttgc | ttcttggcga | gtaaaggaga | ccgaacgaat | gattgctatt | 1320 |
| tgtacagaac | ttagaaagct | gggagcaaca | gtggaggaag | acccgatta | ctgcgtgatc | 1380 |
| accccaccgg | agaagctgaa | cgcgactgca | atcgacacct | acgacgatca | caggatggct | 1440 |
| atggcgttct | ctctcgcagc | ctgtggggat | gtacccgtca | cgatcagaga | ccccggttgc | 1500 |
| acccgcaaaa | ctttcccgga | ctattttgag | gtattgcaga | ggttcacaac | gcactaa | 1557 |

```
<210> SEQ ID NO 6
<211> LENGTH: 518
<212> TYPE: PRT
<213> ORGANISM: Liriope platyphylla
<220> FEATURE:
<221> NAME/KEY: SIGNAL
<222> LOCATION: (1)..(65)
<220> FEATURE:
<221> NAME/KEY: CHAIN
<222> LOCATION: (66)..(518)
<220> FEATURE:
<221> NAME/KEY: ACT_SITE
<222> LOCATION: (146)..(186)
<223> OTHER INFORMATION: Met, Ile, Ala, Met

<400> SEQUENCE: 6

Met Glu Gln Ala Ile Met Ala Lys Gly Val Ala Thr Asn Leu Ser Leu
1               5                   10                  15

Ser Thr Ser Ser Leu Gly Asn Pro Lys Leu Ile Val Ala Ser Ser Ser
            20                  25                  30

Pro Pro Ser Ser Ile Arg Ile Gly Ser Gly Leu Lys Leu Gly Phe
        35                  40                  45

Ser Val Gly Leu Lys Gly Val Gly Met Arg Arg Ala Val Thr Val
    50                  55                  60

Ser Ala Ser Val Ala Ala Ala Glu Lys Pro Ser Thr Val Pro Glu Ile
65                  70                  75                  80

Val Leu Gln Pro Ile Lys Glu Ile Ser Gly Thr Ile Lys Leu Pro Gly
                85                  90                  95

Ser Lys Ser Leu Ser Asn Arg Ile Leu Leu Ala Ala Leu Ala Glu
            100                 105                 110

Gly Thr Thr Val Asp Asn Leu Leu Asp Ser Asp Asp Ile Arg Tyr
            115                 120                 125

Met Leu Ala Ala Leu Lys Thr Leu Gly Leu Ala Val Glu Asp Asp Ser
130                 135                 140

Val Met Lys Arg Ala Thr Val Val Gly Ser Gly Gly Gln Phe Pro Val
145                 150                 155                 160

Gly Lys Asp Ser Lys Glu Val Gln Leu Phe Leu Gly Asn Ala Gly Thr
                165                 170                 175

Ala Met Arg Pro Leu Thr Ala Val Ile Ala Ala Gly Gly Asn Ala
            180                 185                 190

Ser Tyr Ile Leu Asp Gly Val Pro Arg Met Arg Glu Arg Pro Ile Gly
            195                 200                 205

Asp Leu Val Val Gly Leu Lys Gln Leu Gly Ala Asp Val Asp Cys Ile
        210                 215                 220

Leu Gly Ser Asp Cys Pro Pro Val Arg Ala Asn Ala His Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
            260                 265                 270

Glu Ile Met Asp Lys Leu Ile Ser Val Pro Tyr Val Glu Met Thr Leu
        275                 280                 285

Lys Leu Met Glu Arg Phe Gly Val Ser Val Glu His Ser Ser Ser Trp
    290                 295                 300

Asp Arg Phe Phe Ile Lys Gly Gly Gln Lys Tyr Lys Ser Pro Gly Asn
305                 310                 315                 320
```

```
Ala Tyr Val Glu Gly Asp Ala Ser Ser Ser Tyr Phe Leu Ala Gly
                325                 330                 335

Ala Ala Val Thr Gly Gly Thr Val Thr Val Glu Gly Cys Gly Thr Ser
            340                 345                 350

Ser Leu Gln Gly Asp Val Lys Phe Ala Glu Val Leu Glu Lys Met Gly
        355                 360                 365

Ala Lys Val Thr Trp Thr Glu Asn Ser Val Thr Val Thr Gly Pro Pro
    370                 375                 380

Gln Asp Pro Ser Lys Lys Arg Leu Arg Ala Ile Asp Val Asn Met
385                 390                 395                 400

Asn Lys Met Pro Asp Val Ala Met Thr Leu Ala Val Val Ala Leu Tyr
                405                 410                 415

Ala Asp Gly Pro Thr Ala Ile Arg Asp Val Ala Ser Trp Arg Val Lys
            420                 425                 430

Glu Thr Glu Arg Met Ile Ala Ile Cys Thr Glu Leu Arg Lys Leu Gly
        435                 440                 445

Ala Thr Val Glu Glu Gly Pro Asp Tyr Cys Val Ile Thr Pro Pro Glu
    450                 455                 460

Lys Leu Asn Ala Thr Ala Ile Asp Thr Tyr Asp Asp His Arg Met Ala
465                 470                 475                 480

Met Ala Phe Ser Leu Ala Ala Cys Gly Asp Val Pro Val Thr Ile Arg
                485                 490                 495

Asp Pro Gly Cys Thr Arg Lys Thr Phe Pro Asp Tyr Phe Glu Val Leu
            500                 505                 510

Gln Arg Phe Thr Thr His
        515

<210> SEQ ID NO 7
<211> LENGTH: 443
<212> TYPE: PRT
<213> ORGANISM: Liriopes spicata

<400> SEQUENCE: 7

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
        50                  55                  60

Val Glu Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
    130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175
```

```
Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
            195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Thr Val Thr Val Glu
            260                 265                 270

Gly Cys Gly Thr Ser Ser Leu Gln Gly Asp Val Lys Phe Ala Glu Val
            275                 280                 285

Leu Glu Lys Met Gly Ala Lys Val Thr Trp Thr Glu Asn Ser Val Thr
            290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
            355                 360                 365

Leu Arg Lys Leu Gly Ala Thr Val Glu Glu Gly Pro Asp Tyr Cys Val
            370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Arg Asp Pro Gly Cys Thr Arg Lys Thr Phe Pro Asp
            420                 425                 430

Tyr Phe Glu Val Leu Gln Arg Phe Thr Thr His
            435                 440

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Gln Gly Asp Val Arg Phe Ala Glu Val Leu Glu Lys Met Gly Ala
1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Gln Gly Asp Val Lys Tyr Ala Glu Val Leu Glu Lys Met Gly Ala
1               5                  10                  15
```

```
<210> SEQ ID NO 10
<211> LENGTH: 15
<212> TYPE: PRT
<213> ORGANISM: Artificial Sequence
<220> FEATURE:
<223> OTHER INFORMATION: Synthetic Construct

<400> SEQUENCE: 10

Gln Gly Asp Val Lys Phe Ala Glu Val His Glu Lys Met Gly Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Gln Gly Asp Val Arg Tyr Ala Glu Val Leu Glu Lys Met Gly Ala
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Gln Gly Asp Val Arg Phe Ala Glu Val His Glu Lys Met Gly Ala
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Gln Gly Asp Val Lys Tyr Ala Glu Val His Glu Lys Met Gly Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Gln Gly Asp Val Arg Tyr Ala Glu Val His Glu Lys Met Gly Ala
1               5                   10                  15

<210> SEQ ID NO 15
<211> LENGTH: 18
<212> TYPE: PRT
<213> ORGANISM: Artificial Sequence
<220> FEATURE:
<223> OTHER INFORMATION: Synthetic Construct

<400> SEQUENCE: 15

Glu Pro Val Thr Ile Arg Asp Pro Gly Cys Thr Arg Lys Thr Phe Pro
1               5                   10                  15

Asp Tyr
```

```
<210> SEQ ID NO 16
<211> LENGTH: 18
<212> TYPE: PRT
<213> ORGANISM: Artificial Sequence
<220> FEATURE:
<223> OTHER INFORMATION: Synthetic Construct

<400> SEQUENCE: 16

Val Pro Val Thr Ile Gly Asp Pro Gly Cys Thr Arg Lys Thr Phe Pro
1               5                   10                  15

Asp Tyr

<210> SEQ ID NO 17
<211> LENGTH: 18
<212> TYPE: PRT
<213> ORGANISM: Artificial Sequence
<220> FEATURE:
<223> OTHER INFORMATION: Synthetic Construct

<400> SEQUENCE: 17

Val Pro Val Thr Ile Arg Val Pro Gly Cys Thr Arg Lys Thr Phe Pro
1               5                   10                  15

Asp Tyr

<210> SEQ ID NO 18
<211> LENGTH: 18
<212> TYPE: PRT
<213> ORGANISM: Artificial Sequence
<220> FEATURE:
<223> OTHER INFORMATION: Synthetic Construct

<400> SEQUENCE: 18

Val Pro Val Thr Ile Arg Asp Pro Cys Cys Thr Arg Lys Thr Phe Pro
1               5                   10                  15

Asp Tyr

<210> SEQ ID NO 19
<211> LENGTH: 18
<212> TYPE: PRT
<213> ORGANISM: Artificial Sequence
<220> FEATURE:
<223> OTHER INFORMATION: Synthetic Construct

<400> SEQUENCE: 19

Val Pro Val Thr Ile Arg Asp Pro Gly Tyr Thr Arg Lys Thr Phe Pro
1               5                   10                  15

Asp Tyr

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Glu Pro Val Thr Ile Gly Asp Pro Gly Cys Thr Arg Lys Thr Phe Pro
1               5                   10                  15

Asp Tyr

<210> SEQ ID NO 21
<211> LENGTH: 18
<212> TYPE: PRT
```

```
<213> ORGANISM: Artificial Sequence
<220> FEATURE:
<223> OTHER INFORMATION: Synthetic Construct

<400> SEQUENCE: 21

Glu Pro Val Thr Ile Arg Val Pro Gly Cys Thr Arg Lys Thr Phe Pro
1               5                   10                  15

Asp Tyr

<210> SEQ ID NO 22
<211> LENGTH: 18
<212> TYPE: PRT
<213> ORGANISM: Artificial Sequence
<220> FEATURE:
<223> OTHER INFORMATION: Synthetic Construct

<400> SEQUENCE: 22

Val Pro Val Thr Ile Gly Val Pro Gly Cys Thr Arg Lys Thr Phe Pro
1               5                   10                  15

Asp Tyr

<210> SEQ ID NO 23
<211> LENGTH: 18
<212> TYPE: PRT
<213> ORGANISM: Artificial Sequence
<220> FEATURE:
<223> OTHER INFORMATION: Synthetic Construct

<400> SEQUENCE: 23

Val Pro Val Thr Ile Gly Asp Pro Cys Cys Thr Arg Lys Thr Phe Pro
1               5                   10                  15

Asp Tyr

<210> SEQ ID NO 24
<211> LENGTH: 18
<212> TYPE: PRT
<213> ORGANISM: Artificial Sequence
<220> FEATURE:
<223> OTHER INFORMATION: Synthetic Construct

<400> SEQUENCE: 24

Val Pro Val Thr Ile Gly Asp Pro Gly Tyr Thr Arg Lys Thr Phe Pro
1               5                   10                  15

Asp Tyr

<210> SEQ ID NO 25
<211> LENGTH: 18
<212> TYPE: PRT
<213> ORGANISM: Artificial Sequence
<220> FEATURE:
<223> OTHER INFORMATION: Synthetic Construct

<400> SEQUENCE: 25

Val Pro Val Thr Ile Arg Val Pro Gly Tyr Thr Arg Lys Thr Phe Pro
1               5                   10                  15

Asp Tyr

<210> SEQ ID NO 26
<211> LENGTH: 18
<212> TYPE: PRT
<213> ORGANISM: Artificial Sequence
<220> FEATURE:
<223> OTHER INFORMATION: Synthetic Construct
```

```
<400> SEQUENCE: 26

Glu Pro Val Thr Ile Gly Val Pro Gly Cys Thr Arg Lys Thr Phe Pro
1               5                   10                  15

Asp Tyr

<210> SEQ ID NO 27
<211> LENGTH: 18
<212> TYPE: PRT
<213> ORGANISM: Artificial Sequence
<220> FEATURE:
<223> OTHER INFORMATION: Synthetic Construct

<400> SEQUENCE: 27

Glu Pro Val Thr Ile Arg Asp Pro Cys Tyr Thr Arg Lys Thr Phe Pro
1               5                   10                  15

Asp Tyr

<210> SEQ ID NO 28
<211> LENGTH: 18
<212> TYPE: PRT
<213> ORGANISM: Artificial Sequence
<220> FEATURE:
<223> OTHER INFORMATION: Synthetic Construct

<400> SEQUENCE: 28

Val Pro Val Thr Ile Gly Val Pro Cys Cys Thr Arg Lys Thr Phe Pro
1               5                   10                  15

Asp Tyr

<210> SEQ ID NO 29
<211> LENGTH: 443
<212> TYPE: PRT
<213> ORGANISM: Liriopes spicata

<400> SEQUENCE: 29

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Val Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
    50                  55                  60

Val Glu Asn Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
    130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
```

```
                    180                 185                 190
Gly Asp Val Glu Ile Glu Ile Met Asp Lys Leu Ile Ser Val Pro Tyr
                195                 200                 205

Val Glu Met Thr Leu Lys Leu Met Glu Arg Phe Gly Val Ser Val Glu
            210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Thr Val Thr Val Glu
            260                 265                 270

Gly Cys Gly Ser Ser Leu Gln Gly Asp Val Lys Phe Ala Glu Val
        275                 280                 285

Leu Glu Lys Met Gly Ala Lys Val Thr Trp Thr Glu Asn Ser Val Thr
            290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Gly Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
    370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
        435                 440

<210> SEQ ID NO 30
<211> LENGTH: 443
<212> TYPE: PRT
<213> ORGANISM: Liriopes spicata

<400> SEQUENCE: 30

Met Val Pro Glu Ile Val Leu Gln Pro Thr Lys Glu Ile Ser Gly Thr
1               5                   10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
        50                  55                  60

Val Glu Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110
```

-continued

```
Ala Gly Gly Asn Ala Ser Tyr Ile Leu Asp Gly Val Pro Arg Met Arg
            115                 120                 125

Glu Arg Pro Ile Gly Asp Leu Val Val Gly Leu Lys Gln Leu Gly Ala
        130                 135                 140

Asp Val Asp Cys Ile Leu Gly Thr Asp Cys Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Gln Leu Ile Ser Val Pro Tyr
        195                 200                 205

Val Glu Met Thr Leu Lys Leu Met Glu Arg Phe Gly Val Ser Val Glu
    210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Thr Val Thr Ala Glu
            260                 265                 270

Gly Cys Gly Thr Ser Ser Leu Gln Gly Asp Val Lys Phe Ala Glu Val
        275                 280                 285

Leu Glu Lys Met Gly Ala Lys Val Thr Trp Thr Glu Asn Ser Val Thr
    290                 295                 300

Val Thr Gly Ser Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
    370                 375                 380

Ile Thr Pro Pro Glu Lys Leu Asn Ala Asn Ala Ile Val Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
        435                 440

<210> SEQ ID NO 31
<211> LENGTH: 443
<212> TYPE: PRT
<213> ORGANISM: Liriopes spicata

<400> SEQUENCE: 31

Met Val Pro Glu Ile Val Leu Gln Pro Ile Lys Glu Ile Ser Gly Thr
1               5                   10                  15

Ile Lys Leu Pro Gly Ser Lys Ser Leu Ser Tyr Arg Ile Leu Leu Leu
            20                  25                  30

Ala Ala Leu Ala Glu Gly Thr Thr Val Val Asp Asn Leu Leu Asp Ser
        35                  40                  45
```

Asp Asp Ile Arg Tyr Met Leu Ala Ala Leu Lys Thr Leu Gly Leu Thr
50                  55                  60

Val Glu Asp Asp Ser Val Met Lys Arg Ala Thr Val Val Gly Ser Gly
65                  70                  75                  80

Gly Leu Phe Pro Val Gly Lys Asp Ser Asn Glu Val His Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Val Ile Met Asp Lys Leu Ile Ser Val Pro Tyr
        195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Lys Phe Ala Glu Val
        275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Gly Ile Arg Asp Val Ala
            340                 345                 350

Ser Trp Arg Val Lys Glu Thr Glu Arg Met Ile Ala Ile Arg Thr Glu
        355                 360                 365

Leu Arg Lys Leu Gly Ala Thr Val Glu Glu Gly Pro Asp Tyr Cys Val
370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Tyr Thr Arg Lys Thr Phe Pro Asp
            420                 425                 430

Tyr Phe Glu Val Leu Gln Arg Phe Thr Thr His
        435                 440

<210> SEQ ID NO 32
<211> LENGTH: 443

<212> TYPE: PRT
<213> ORGANISM: Liriopes spicata

<400> SEQUENCE: 32

```
Met Glu Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
    50                  55                  60

Val Glu Asp Asp Arg Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
    130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Phe
        195                 200                 205

Val Glu Met Thr Leu Lys Leu Met Glu Arg Phe Gly Val Ser Val Glu
    210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Gly Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Ile Glu Asn Ser Val Thr
    290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
    370                 375                 380

Ile Thr Pro Pro Glu Lys Leu Asn Ala Asn Ala Ile Asp Thr Tyr Asp
385                 390                 395                 400
```

```
Asp His Arg Met Ala Met Ala Phe Ser Leu Ala Ala Cys Ala Asp Val
            405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
            435                 440
```

<210> SEQ ID NO 33
<211> LENGTH: 443
<212> TYPE: PRT
<213> ORGANISM: Liriopes spicata

<400> SEQUENCE: 33

```
Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
50                  55                  60

Val Glu Asp Asp Ser Ala Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Trp Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
```

```
                    325                 330                 335
Val Val Ala Leu Tyr Ala Asp Gly Pro Thr Ala Ile Arg Asp Val Ala
                340                 345                 350

Ser Trp Arg Val Lys Glu Thr Glu Arg Met Ile Ala Ile Cys Thr Glu
            355                 360                 365

Leu Arg Lys Leu Gly Ala Thr Val Glu Glu Gly Pro Asp Tyr Cys Val
        370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
                420                 425                 430

Tyr Phe Glu Val Leu Gln Arg Phe Thr Thr His
            435                 440

<210> SEQ ID NO 34
<211> LENGTH: 443
<212> TYPE: PRT
<213> ORGANISM: Liriopes spicata

<400> SEQUENCE: 34

Met Val Pro Glu Ile Val Leu Gln Pro Ile Lys Glu Ile Ser Gly Thr
1               5                   10                  15

Ile Lys Leu Pro Gly Ser Lys Ser Leu Ser Tyr Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
    50                  55                  60

Val Glu Asp Asp Arg Val Met Lys Arg Ala Thr Val Val Gly Ser Gly
65                  70                  75                  80

Gly Leu Phe Pro Val Gly Lys Asp Ser Asn Glu Val His Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
    130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Val Ile Met Asp Lys Leu Ile Ser Val Pro Tyr
        195                 200                 205

Val Glu Met Thr Leu Lys Leu Met Glu Arg Phe Gly Val Ser Val Glu
    210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255
```

```
Tyr Phe Leu Ala Gly Ala Ala Val Thr Gly Gly Thr Val Thr Val Glu
                260                 265                 270

Gly Cys Gly Thr Ser Ser Leu Gln Gly Asp Val Arg Phe Ala Glu Val
            275                 280                 285

Leu Glu Lys Met Gly Ala Lys Val Thr Trp Thr Glu Asn Ser Val Thr
        290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Gly Ile Arg Asp Val Ala
                340                 345                 350

Ser Trp Arg Val Lys Glu Thr Glu Arg Met Ile Ala Ile Arg Thr Glu
            355                 360                 365

Leu Arg Lys Leu Gly Ala Thr Val Glu Glu Gly Pro Asp Tyr Cys Val
        370                 375                 380

Ile Thr Pro Pro Glu Lys Leu Asn Ala Asn Ala Ile Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Tyr Thr Arg Lys Thr Phe Pro Asp
                420                 425                 430

Tyr Phe Glu Val Leu Gln Arg Phe Thr Thr His
            435                 440

<210> SEQ ID NO 35
<211> LENGTH: 443
<212> TYPE: PRT
<213> ORGANISM: Liriopes spicata

<400> SEQUENCE: 35

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
    50                  55                  60

Val Glu Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Gly Leu Lys Gln Leu Gly Ala
    130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190
```

```
Gly Asp Val Glu Ile Glu Ile Met Asp Lys Leu Ile Ser Val Pro Tyr
            195                 200                 205
Val Glu Met Thr Leu Lys Leu Met Glu Arg Phe Gly Val Ser Val Glu
210                 215                 220
His Ser Ser Trp Asp Arg Phe Phe Ile Lys Gly Gly Gln Lys Tyr
225                 230                 235                 240
Lys Ser Pro Gly Asn Ala Tyr Val Glu Gly Asp Ala Ser Ser Ala Ser
            245                 250                 255
Tyr Phe Leu Ala Gly Ala Ala Val Thr Gly Thr Val Thr Val Glu
            260                 265                 270
Gly Cys Gly Thr Ser Ser Leu Gln Gly Asp Val Arg Phe Ala Glu Val
            275                 280                 285
Leu Glu Lys Met Gly Ala Lys Val Thr Trp Thr Glu Asn Ser Val Thr
            290                 295                 300
Val Thr Gly Pro Pro Gln Asp Pro Ser Lys Lys Arg Leu Arg Ala
305                 310                 315                 320
Val Asp Val Asn Met Asn Lys Met Pro Asp Val Ala Met Thr Leu Ala
            325                 330                 335
Val Val Ala Leu Tyr Ala Asp Gly Pro Thr Ala Ile Arg Asp Val Ala
            340                 345                 350
Ser Trp Arg Val Lys Glu Thr Glu Arg Met Ile Ala Ile Cys Thr Glu
            355                 360                 365
Leu Arg Lys Leu Gly Ala Thr Val Glu Glu Gly Pro Asp Tyr Cys Val
            370                 375                 380
Ile Thr Pro Pro Glu Lys Leu Asn Ala Asn Ala Ile Asp Thr Tyr Asp
385                 390                 395                 400
Asp His Arg Met Ala Met Ala Phe Ser Leu Ala Ala Cys Ala Asp Val
            405                 410                 415
Pro Val Thr Ile Gly Asp Pro Gly Cys Thr Arg Lys Thr Phe Pro Asp
            420                 425                 430
Tyr Phe Glu Val Leu Gln Arg Phe Thr Thr His
            435                 440

<210> SEQ ID NO 36
<211> LENGTH: 443
<212> TYPE: PRT
<213> ORGANISM: Liriopes spicata

<400> SEQUENCE: 36

Met Val Pro Glu Ile Val Leu Gln Pro Ile Lys Glu Ile Ser Gly Thr
1               5                   10                  15
Ile Lys Leu Pro Gly Ser Lys Ser Leu Ser Asn Arg Ile Leu Leu Leu
            20                  25                  30
Ala Ala Leu Ala Glu Gly Thr Thr Val Val Asp Asn Leu Leu Asp Ser
            35                  40                  45
Asp Asp Ile Arg Tyr Met Leu Ala Ala Leu Lys Thr Leu Gly Leu Thr
        50                  55                  60
Val Glu Asp Asp Arg Val Met Lys Arg Ala Thr Val Val Gly Ser Gly
65                  70                  75                  80
Gly Gln Phe Pro Val Gly Lys Asp Ser Lys Glu Val Gln Leu Phe Leu
            85                  90                  95
Gly Asn Ala Gly Thr Ala Met Arg Pro Leu Thr Ala Ala Val Ile Ala
            100                 105                 110
Ala Gly Gly Asn Ala Ser Tyr Ile Leu Asp Gly Val Pro Arg Met Arg
```

```
            115                 120                 125
Glu Arg Pro Ile Gly Asp Leu Val Val Gly Leu Lys Gln Leu Gly Ala
    130                 135                 140

Asp Val Asp Cys Ile Leu Gly Thr Asp Cys Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Val Thr Leu Lys Leu Met Glu Arg Phe Gly Val Ser Val Glu
    210                 215                 220

His Ser Ser Ser Trp Asp Arg Phe Phe Ile Lys Gly Gly Gln Lys Tyr
225                 230                 235                 240

Lys Ser Pro Gly Asn Ala Cys Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
    290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Val Arg Asp Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
    370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
        435                 440

<210> SEQ ID NO 37
<211> LENGTH: 443
<212> TYPE: PRT
<213> ORGANISM: Liriopes spicata

<400> SEQUENCE: 37

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Cys
        35                  40                  45
```

```
Asp Asp Ile Arg Tyr Met Leu Ala Ala Leu Lys Thr Leu Gly Leu Thr
 50                  55                  60

Val Glu Asp Asp Ser Val Met Lys Arg Ala Thr Val Val Gly Ser Gly
 65                  70                  75                  80

Gly Gln Phe Pro Val Gly Lys Asp Ser Lys Glu Val Gln Leu Phe Leu
                 85                  90                  95

Gly Asn Ala Gly Thr Ala Met Arg Pro Leu Thr Ala Ala Val Ile Ala
                100                 105                 110

Ala Gly Gly Asn Ala Ser Tyr Ile Leu Asp Gly Val Pro Arg Met Arg
             115                 120                 125

Glu Arg Pro Ile Gly Asp Leu Val Ile Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Glu Val Lys Leu Ser Gly Ser Ile
                165                 170                 175

Ser Ser Gln Tyr Leu Thr Ala Leu Leu Met Ala Ala Pro Leu Ala Leu
             180                 185                 190

Gly Asp Val Glu Ile Glu Ile Met Asp Lys Leu Ile Ser Val Pro Tyr
             195                 200                 205

Val Glu Met Thr Leu Lys Leu Met Glu Arg Phe Gly Val Ser Val Glu
210                 215                 220

His Ser Ser Ser Trp Asp Arg Phe Phe Ile Met Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
             260                 265                 270

Gly Cys Gly Thr Ser Ser Leu Gln Gly Asp Val Arg Phe Ala Glu Val
         275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
             340                 345                 350

Ser Trp Arg Val Lys Glu Thr Glu Arg Met Ile Ala Ile Cys Thr Glu
         355                 360                 365

Leu Arg Lys Leu Gly Ala Thr Val Glu Glu Gly Pro Asp Tyr Cys Val
370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
             420                 425                 430

Tyr Phe Glu Val Leu Gln Arg Phe Thr Thr His
             435                 440

<210> SEQ ID NO 38
<211> LENGTH: 443
<212> TYPE: PRT
```

-continued

<213> ORGANISM: Liriopes spicata

<400> SEQUENCE: 38

```
Met Val Pro Glu Ile Val Leu Gln Pro Ile Lys Glu Ile Ser Gly Thr
 1               5                  10                  15

Ile Lys Leu Pro Gly Ser Lys Ser Leu Ser Asn Arg Ile Leu Leu Leu
             20                  25                  30

Ala Ala Leu Ala Glu Gly Thr Thr Val Val Asp Asn Leu Leu Asp Ser
         35                  40                  45

Asp Asp Ile Arg Tyr Met Leu Ala Ala Leu Lys Thr Leu Gly Leu Thr
     50                  55                  60

Val Glu Asp Asp Ser Val Met Lys Arg Ala Thr Val Val Gly Ser Gly
 65                  70                  75                  80

Gly Gln Phe Pro Val Gly Lys Asp Ser Lys Glu Val Gln Leu Phe Leu
                 85                  90                  95

Gly Asn Ala Gly Thr Ala Met Arg Pro Leu Thr Ala Ala Val Ile Ala
            100                 105                 110

Ala Gly Gly Asn Ala Ser Tyr Leu Leu Asp Gly Val Pro Arg Met Arg
        115                 120                 125

Glu Arg Pro Ile Gly Asp Leu Val Val Gly Leu Lys Gln Leu Gly Ala
    130                 135                 140

Asp Val Asp Cys Ile Leu Gly Thr Asp Cys Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Thr Leu Lys Leu Met Glu Arg Phe Gly Val Ser Val Glu
    210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
    290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Val Met Thr Leu Ala
                325                 330                 335

Val Val Ala Pro Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
    370                 375                 380

Ile Thr Pro Pro Val Lys Leu Asn Ala Asn Ala Ile Asp Thr Tyr Asp
385                 390                 395                 400
```

Asp His Arg Met Ala Met Ala Phe Ser Leu Ala Ala Cys Ala Asp Val
              405                 410                 415

Pro Val Thr Ile Gly Asp Pro Gly Cys Thr Arg Lys Thr Phe Pro Asp
              420                 425                 430

Tyr Phe Glu Val Leu Gln Arg Phe Thr Thr His
              435                 440

<210> SEQ ID NO 39
<211> LENGTH: 443
<212> TYPE: PRT
<213> ORGANISM: Liriopes spicata

<400> SEQUENCE: 39

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
50                  55                  60

Val Gly Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
    130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Thr Leu Lys Leu Met Glu Arg Phe Gly Val Ser Val Gly
    210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
    290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

```
Val Val Ala Leu Tyr Ala Asp Gly Pro Thr Ala Ile Arg Asp Val Ala
            340                 345                 350

Thr Trp Arg Val Lys Glu Thr Glu Arg Met Ile Ala Ile Cys Thr Glu
            355                 360                 365

Leu Arg Lys Leu Gly Ala Thr Val Glu Glu Gly Pro Asp Tyr Cys Val
            370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
            405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
            435                 440

<210> SEQ ID NO 40
<211> LENGTH: 443
<212> TYPE: PRT
<213> ORGANISM: Liriopes spicata

<400> SEQUENCE: 40

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
50                  55                  60

Val Val Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
            85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
            115                 120                 125

Glu Arg Pro Ile Gly Asp Leu Val Val Gly Leu Lys Gln Leu Gly Ala
            130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
            165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
            195                 200                 205

Val Glu Met Thr Leu Lys Leu Met Glu Arg Phe Gly Val Ser Val Glu
            210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
            245                 250                 255

Tyr Phe Leu Ala Gly Ala Ala Val Thr Gly Gly Thr Val Thr Val Glu
```

```
                260                 265                 270
Gly Cys Gly Thr Ser Ser Leu Gln Gly Asp Val Arg Phe Ala Glu Val
            275                 280                 285
Leu Glu Lys Met Gly Ala Lys Val Thr Trp Thr Glu Asn Ser Val Thr
        290                 295                 300
Val Thr Gly Pro Pro Gln Asp Pro Ser Lys Lys Arg Leu Arg Ala
305                 310                 315                 320
Val Asp Val Asn Met Asn Lys Met Pro Asp Val Ala Met Thr Leu Ala
                325                 330                 335
Val Val Ala Leu Tyr Ala Asp Gly Pro Thr Ala Ile Arg Asp Val Ala
            340                 345                 350
Ser Trp Arg Val Lys Glu Thr Glu Arg Met Ile Ala Ile Cys Thr Glu
        355                 360                 365
Leu Arg Met Leu Gly Ala Thr Val Glu Glu Gly Pro Asp Tyr Cys Val
    370                 375                 380
Ile Thr Pro Pro Glu Lys Leu Asn Ala Asn Ala Ile Asp Thr Tyr Asp
385                 390                 395                 400
Gly His Arg Met Ala Met Ala Phe Ser Leu Ala Ala Cys Ala Asp Val
                405                 410                 415
Pro Val Thr Ile Gly Asp Pro Gly Cys Thr Arg Lys Thr Phe Pro Asp
            420                 425                 430
Tyr Phe Glu Val Leu Gln Arg Phe Thr Thr His
        435                 440

<210> SEQ ID NO 41
<211> LENGTH: 443
<212> TYPE: PRT
<213> ORGANISM: Liriopes spicata

<400> SEQUENCE: 41

Met Val Pro Glu Ile Val Leu Gln Pro Ile Lys Glu Ile Ser Gly Thr
1               5                   10                  15
Ile Lys Leu Pro Gly Ser Lys Ser Leu Ser Asn Arg Ile Leu Leu Leu
            20                  25                  30
Ala Ala Leu Ala Glu Gly Thr Thr Val Val Asp Asn Leu Leu Asp Ser
        35                  40                  45
Asp Asp Ile Arg Tyr Met Leu Ala Ala Leu Lys Thr Leu Gly Leu Thr
    50                  55                  60
Val Glu Asp Asp Ser Val Met Lys Arg Ala Thr Val Val Gly Ser Gly
65                  70                  75                  80
Gly Gln Phe Pro Val Gly Lys Asp Ser Lys Glu Val Gln Leu Phe Leu
                85                  90                  95
Gly Asn Ala Gly Thr Ala Met Arg Pro Leu Thr Ala Ala Val Ile Ala
            100                 105                 110
Ala Gly Gly Asn Ala Ser Tyr Ile Leu Asp Gly Val Pro Arg Met Arg
        115                 120                 125
Glu Arg Pro Ile Gly Asp Leu Val Val Gly Leu Lys Gln Leu Gly Ala
    130                 135                 140
Asp Val Asp Cys Ile Leu Gly Thr Asp Cys Pro Pro Val Arg Ala Asn
145                 150                 155                 160
Ala His Gly Gly Leu Pro Gly Gly Arg Val Lys Leu Ser Gly Ser Ile
                165                 170                 175
Ser Ser Gln Tyr Leu Thr Ala Leu Leu Met Ala Ala Pro Leu Ala Leu
            180                 185                 190
```

-continued

```
Gly Asp Val Glu Ile Glu Ile Met Asp Lys Leu Ile Ser Val Pro Tyr
            195                 200                 205

Val Glu Met Thr Leu Lys Leu Met Glu Arg Phe Gly Val Ser Val Glu
        210                 215                 220

His Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Ala Gly Thr Val Thr Val Gly
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Tyr Ser Val Thr
    290                 295                 300

Val Thr Gly Pro Pro Arg Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
    370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
        435                 440

<210> SEQ ID NO 42
<211> LENGTH: 443
<212> TYPE: PRT
<213> ORGANISM: Liriopes spicata

<400> SEQUENCE: 42

Met Val Pro Glu Ile Val Leu Gln Pro Ile Lys Glu Ile Ser Gly Thr
1               5                   10                  15

Ile Lys Leu Pro Gly Ser Lys Ser Leu Ser Tyr Arg Ile Leu Leu Leu
            20                  25                  30

Ala Ala His Ala Glu Gly Thr Thr Val Val Asp Asn Leu Leu Asp Gly
        35                  40                  45

Asp Asp Ile Arg Tyr Met Leu Ala Ala Leu Lys Thr Leu Gly Leu Thr
    50                  55                  60

Val Glu Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125
```

```
Glu Arg Pro Ile Gly Asp Leu Val Gly Leu Lys Gln Leu Gly Ala
    130                 135                 140

Asp Val Asp Cys Ile Leu Gly Thr Asp Cys Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Asn Leu Ile Ser Val Pro Tyr
            195                 200                 205

Val Glu Met Thr Leu Lys Leu Met Glu Arg Phe Gly Val Ser Val Glu
    210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
            275                 280                 285

Leu Glu Lys Met Gly Ala Lys Val Thr Trp Thr Glu Asn Ser Val Thr
    290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
    355                 360                 365

Leu Arg Lys Leu Gly Ala Thr Val Glu Glu Gly Pro Asp Tyr Cys Val
    370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Leu Glu Val Leu Gln Arg Phe Thr Thr His
            435                 440

<210> SEQ ID NO 43
<211> LENGTH: 443
<212> TYPE: PRT
<213> ORGANISM: Liriopes spicata

<400> SEQUENCE: 43

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Lys Leu Leu Asp Ser
            35                  40                  45

Asp Asp Ile Arg Tyr Met Leu Ala Ala Leu Lys Thr Leu Gly Leu Thr
```

```
                50                  55                  60
Val Glu Asp Asp Ser Val Met Lys Arg Ala Thr Val Val Gly Ser Gly
 65                  70                  75                  80

Gly Gln Phe Pro Val Gly Lys Asp Ser Lys Glu Val Gln Leu Phe Leu
                 85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
            115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Val Arg Ala Asn
145                 150                 155                 160

Ala His Gly Gly Leu Pro Gly Gly Thr Val Lys Leu Ser Gly Ser Ile
            165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
            195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asn Ala Ser Ser Ala Ser
            245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
            275                 280                 285

Leu Glu Lys Met Gly Ala Lys Val Thr Trp Thr Glu Asn Ser Val Thr
290                 295                 300

Val Thr Gly Thr Pro Gln Asp Pro Ser Lys Lys Arg Leu Arg Ala
305                 310                 315                 320

Val Asp Val Asn Met Asn Lys Met Pro Asp Val Ala Met Thr Leu Ala
            325                 330                 335

Val Val Ala Leu Tyr Ala Asp Gly Pro Thr Ala Ile Arg Asp Val Ala
            340                 345                 350

Thr Trp Arg Val Lys Glu Thr Glu Arg Met Ile Ala Ile Cys Thr Glu
            355                 360                 365

Leu Arg Lys Leu Gly Ala Thr Val Glu Glu Gly Pro Asp Tyr Cys Val
370                 375                 380

Ile Thr Pro Pro Glu Lys Leu Asn Ala Tyr Ala Ile Asp Thr Tyr Asp
385                 390                 395                 400

Asp His Arg Met Ala Met Ala Phe Ser Leu Ala Ala Cys Ala Asp Val
            405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
            435                 440

<210> SEQ ID NO 44
<211> LENGTH: 443
<212> TYPE: PRT
<213> ORGANISM: Liriopes spicata
```

<400> SEQUENCE: 44

```
Met Val Pro Glu Ile Val Leu Gln Pro Ile Lys Glu Ile Ser Gly Thr
1               5                   10                  15
Ile Lys Leu Pro Gly Ser Lys Ser Leu Ser Asn Arg Ile Leu Leu Leu
            20                  25                  30
Ala Ala Leu Ala Glu Gly Thr Thr Val Asp Asn Leu Leu Asp Ser
        35                  40                  45
Asp Asp Ile Arg Tyr Met Leu Ala Ala Leu Lys Thr Leu Gly Leu Thr
    50                  55                  60
Val Glu Asp Asp Ser Val Met Lys Arg Ala Thr Val Val Gly Ser Gly
65                  70                  75                  80
Gly Gln Phe Pro Val Gly Lys Asp Ser Lys Glu Val Gln Leu Phe Leu
                85                  90                  95
Gly Asn Ala Gly Thr Ala Met Arg Pro Leu Thr Ala Ala Val Ile Ala
            100                 105                 110
Ala Gly Gly Asn Ala Ser Tyr Ile Leu Asp Gly Val Pro Arg Met Arg
        115                 120                 125
Glu Arg Pro Ile Gly Asp Leu Val Val Gly Leu Lys Gln Leu Gly Ala
    130                 135                 140
Asp Val Asp Cys Ile Leu Gly Thr Asp Cys Pro Pro Val Arg Ala Asn
145                 150                 155                 160
Ala His Gly Gly Leu Pro Gly Gly Lys Val Lys Leu Ser Gly Ser Ile
                165                 170                 175
Ser Ser Gln Tyr Leu Thr Ala Leu Leu Met Ala Ala Pro Leu Ala Leu
            180                 185                 190
Gly Asp Val Glu Ile Glu Ile Met Asp Lys Leu Ile Ser Val Pro Tyr
        195                 200                 205
Val Glu Met Thr Leu Lys Leu Met Glu Arg Phe Gly Val Ser Val Glu
    210                 215                 220
His Ser Ser Ser Trp Asp Arg Phe Phe Ile Lys Gly Gly Gln Lys Tyr
225                 230                 235                 240
Lys Ser Pro Gly Asn Ala Tyr Val Glu Gly Asp Ala Ser Ser Ala Ser
                245                 250                 255
Tyr Phe Leu Ala Gly Ala Ala Val Thr Gly Gly Thr Val Thr Val Glu
            260                 265                 270
Gly Cys Gly Thr Ser Ser Leu Gln Gly Asp Val Arg Tyr Ala Glu Val
        275                 280                 285
His Glu Lys Met Gly Ala Lys Val Thr Trp Thr Glu Asn Ser Val Thr
    290                 295                 300
Val Thr Gly Pro Pro Gln Asp Pro Ser Lys Lys Lys Arg Leu Arg Ala
305                 310                 315                 320
Val Asp Val Asn Leu Asn Lys Met Pro Asp Val Ala Met Thr Leu Ala
                325                 330                 335
Val Val Ala Leu Tyr Ala Asp Gly Pro Thr Ala Ile Arg Asp Val Ala
            340                 345                 350
Ser Trp Arg Val Lys Glu Thr Glu Arg Met Ile Ala Ile Cys Thr Glu
        355                 360                 365
Leu Arg Lys Leu Gly Ala Thr Val Glu Asp Gly Pro Asp Tyr Cys Val
    370                 375                 380
Ile Thr Pro Pro Glu Lys Leu Asn Ala Asn Ala Ile Asp Ser Tyr Asp
385                 390                 395                 400
Asp His Arg Met Ala Met Ala Phe Ser Leu Ala Ala Cys Ala Asp Val
```

```
                    405                 410                 415
Pro Val Thr Ile Gly Asp Pro Gly Cys Thr Arg Lys Thr Phe Pro Asp
                420                 425                 430

Tyr Phe Glu Val Leu Gln Arg Phe Thr Thr His
            435                 440
```

<210> SEQ ID NO 45
<211> LENGTH: 443
<212> TYPE: PRT
<213> ORGANISM: Liriopes spicata

<400> SEQUENCE: 45

```
Met Val Pro Glu Ile Val Leu Gln Pro Ile Lys Glu Ile Ser Gly Thr
 1               5                  10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Asn Leu Leu Asp Ser
            35                  40                  45

Val Asp Ile Arg Tyr Met Leu Ala Ala Leu Lys Thr Leu Gly Leu Thr
        50                  55                  60

Val Glu Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Val Leu Asp Gly Val Pro Arg Met Arg
        115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Thr Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Ile Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Lys
290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335
```

```
Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
            355                 360                 365

Leu Arg Lys Leu Gly Ala Thr Val Glu Glu Gly Pro Asp Tyr Cys Val
            370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Glu
            405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
            435                 440

<210> SEQ ID NO 46
<211> LENGTH: 443
<212> TYPE: PRT
<213> ORGANISM: Liriopes spicata

<400> SEQUENCE: 46

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
            35                  40                  45

Asp Asp Val Arg Tyr Met Leu Ala Ala Leu Arg Thr Leu Gly Leu Thr
50                  55                  60

Val Glu Asp Asp Ser Val Met Lys Arg Ala Thr Val Val Gly Ser Gly
65                  70                  75                  80

Gly Gln Phe Pro Val Gly Lys Asp Ser Lys Glu Val Gln Leu Leu Leu
            85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
            115                 120                 125

Glu Arg Pro Ile Gly Asp Leu Val Val Gly Leu Lys Gln Leu Gly Ala
            130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
            165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
            195                 200                 205

Val Glu Met Thr Leu Lys Leu Met Glu Arg Phe Gly Val Ser Val Glu
            210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
            245                 250                 255

Tyr Phe Leu Ala Gly Ala Ala Val Thr Gly Gly Thr Val Thr Val Glu
            260                 265                 270
```

Gly Cys Gly Thr Ser Ser Leu Gln Gly Asp Val Arg Phe Ala Glu Val
            275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Arg Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
                340                 345                 350

Ser Trp Arg Val Lys Glu Thr Glu Arg Met Ile Ala Ile Cys Thr Glu
                355                 360                 365

Leu Arg Lys Leu Gly Ala Thr Val Glu Glu Gly Pro Asp Tyr Cys Val
370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
                420                 425                 430

Tyr Phe Glu Val Leu Gln Arg Phe Thr Thr His
            435                 440

<210> SEQ ID NO 47
<211> LENGTH: 443
<212> TYPE: PRT
<213> ORGANISM: Liriopes spicata

<400> SEQUENCE: 47

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
50                  55                  60

Val Glu Asp Asp Ser Val Met Lys Pro Ala Thr Val Val Gly Ser Gly
65                  70                  75                  80

Gly Gln Phe Pro Val Gly Lys Val Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
        130                 135                 140

Asp Val Asp Cys Ile Leu Gly Thr Asp Ser Pro Pro Val Arg Ala Asn
145                 150                 155                 160

Ala His Gly Gly Leu Pro Gly Gly Lys Val Lys Leu Ser Gly Ser Ile
                165                 170                 175

Ser Cys Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr

```
                    195                 200                 205
Val Glu Lys Thr Leu Lys Leu Met Glu Arg Phe Gly Val Ser Val Glu
210                 215                 220

His Ser Ser Ser Trp Asp Arg Phe Phe Asn Lys Gly Gly Gln Lys Tyr
225                 230                 235                 240

Lys Ser Pro Gly Asn Ala Tyr Val Glu Gly Glu Ala Ser Ser Ala Ser
            245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
            275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
                340                 345                 350

Ser Trp Arg Val Lys Gly Thr Glu Arg Met Ile Ala Ile Cys Thr Glu
            355                 360                 365

Leu Arg Lys Leu Gly Ala Thr Val Glu Glu Gly Pro Asp Tyr Cys Val
            370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
                420                 425                 430

Tyr Phe Glu Val Leu Gln Arg Phe Thr Thr His
            435                 440

<210> SEQ ID NO 48
<211> LENGTH: 443
<212> TYPE: PRT
<213> ORGANISM: Liriopes spicata

<400> SEQUENCE: 48

Met Val Pro Glu Ile Val Leu Gln Pro Ile Lys Glu Ile Ser Gly Thr
1               5                   10                  15

Ile Lys Leu Pro Gly Ser Lys Thr Leu Ser Asn Arg Ile Leu Leu Leu
                20                  25                  30

Ala Ser Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
50                  55                  60

Val Glu Asp Asp Ser Val Met Lys Arg Val Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
            115                 120                 125
```

```
Glu Arg Pro Ile Arg Asp Leu Val Val Gly Leu Lys Gln Leu Gly Ala
130                 135                 140

Asp Val Asp Cys Ile Leu Gly Thr Asp Cys Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
                195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Val Thr Gly Gly Thr Val Thr Val Glu
            260                 265                 270

Gly Cys Gly Thr Ser Ser Leu Gln Gly Asp Val Arg Phe Ala Glu Val
            275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Arg Leu Arg Ala
305                 310                 315                 320

Val Asp Asp Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
            355                 360                 365

Leu Arg Lys Leu Gly Ala Thr Val Glu Glu Gly Pro Asp Tyr Cys Val
            370                 375                 380

Ile Thr Thr Pro Val Lys Leu Asn Ala Asn Ala Ile Asp Thr Tyr Asp
385                 390                 395                 400

Asp His Arg Met Ala Met Ala Phe Ser Leu Ala Ala Cys Ala Asp Leu
                405                 410                 415

Pro Val Thr Ile Gly Val Pro Gly Cys Thr Arg Lys Thr Phe Pro Asp
                420                 425                 430

Tyr Phe Glu Val Leu Gln Arg Phe Thr Thr His
            435                 440

<210> SEQ ID NO 49
<211> LENGTH: 443
<212> TYPE: PRT
<213> ORGANISM: Liriopes spicata

<400> SEQUENCE: 49

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
50                  55                  60
```

Val Glu Asp Asp Ser Val Met Lys Arg Ala Thr Val Val Gly Ser Gly
 65                  70                  75                  80

Gly Gln Phe Pro Val Gly Lys Asp Ser Lys Glu Val Gln Leu Phe Leu
                 85                  90                  95

Gly Asn Ala Gly Thr Ala Met Arg Pro Leu Thr Ala Ala Val Ile Ala
            100                 105                 110

Ala Gly Gly Asn Thr Ser Tyr Ile Leu Asp Gly Val Pro Arg Met Arg
        115                 120                 125

Glu Arg Pro Ile Gly Asp Leu Val Gly Leu Lys Gln Leu Gly Ala
130                 135                 140

Asp Val Asp Cys Ile Leu Gly Thr Asp Cys Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Ser Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
        355                 360                 365

Leu Arg Lys Leu Gly Ala Thr Val Glu Glu Gly Pro Asp Tyr Cys Val
370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Pro Thr His
        435                 440

<210> SEQ ID NO 50
<211> LENGTH: 443
<212> TYPE: PRT
<213> ORGANISM: Liriopes spicata

<400> SEQUENCE: 50

```
Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
    50                  55                  60

Val Glu Asp Asp Ser Val Met Lys Arg Ala Ser Val Val Gly Ser Gly
65                  70                  75                  80

Gly Gln Phe Pro Val Gly Arg Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Ser Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Ser Glu Arg Lys Ile Ala Ile Cys Thr Glu
        355                 360                 365

Leu Arg Lys Leu Gly Ala Thr Val Glu Glu Gly Pro Asp Tyr Cys Val
370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415
```

Pro Val Thr Ile Gly Asp Pro Gly Cys Thr Arg Lys Thr Phe Pro Asp
                420                 425                 430

Tyr Phe Glu Val Leu Gln Arg Phe Thr Thr His
            435                 440

<210> SEQ ID NO 51
<211> LENGTH: 443
<212> TYPE: PRT
<213> ORGANISM: Liriopes spicataLiriopes spicata

<400> SEQUENCE: 51

Met Val Pro Glu Ile Val Leu Gln Pro Ile Lys Glu Ile Ser Gly Thr
1               5                   10                  15

Ile Lys Leu Pro Gly Ser Lys Ser Leu Ser Asn Arg Ile Leu Leu Leu
                20                  25                  30

Ala Ala Leu Ala Glu Gly Thr Thr Val Val Asp Asn Leu Leu Asp Ser
            35                  40                  45

Asp Asp Ile Arg Tyr Met Leu Ala Ala Leu Lys Thr Leu Gly Leu Thr
    50                  55                  60

Val Glu Asp Gly Ser Val Met Lys Arg Ala Thr Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Val Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
                165                 170                 175

Ser Ser Gln Tyr Leu Thr Ala Leu Leu Met Ala Ala Pro Leu Ala Leu
            180                 185                 190

Gly Asp Val Glu Ile Glu Ile Met Asp Lys Leu Ile Ser Val Pro Tyr
        195                 200                 205

Val Glu Met Thr Leu Lys Leu Met Glu Arg Phe Gly Val Ser Val Glu
210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270

Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
    290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Gly Asp Val Ala

```
                340              345                350
Ser Trp Arg Val Lys Glu Thr Glu Arg Met Ile Ala Ile Cys Thr Glu
            355                360                365

Leu Arg Lys Leu Gly Ala Thr Val Glu Glu Gly Pro Asp Tyr Cys Val
        370                375                380

Ile Thr Pro Pro Glu Lys Leu Asn Ala Asn Ala Ile Asp Thr Tyr Asp
385                390                395                400

Asp His Arg Met Ala Met Ala Phe Ser Leu Ala Ala Cys Ala Asp Val
            405                410                415

Pro Val Thr Ile Gly Asp Pro Cys Cys Thr Arg Lys Thr Phe Pro Asp
        420                425                430

Tyr Phe Glu Val Leu Gln Arg Phe Thr Thr His
            435                440

<210> SEQ ID NO 52
<211> LENGTH: 443
<212> TYPE: PRT
<213> ORGANISM: Liriopes spicata

<400> SEQUENCE: 52

Met Val Pro Glu Ile Val Leu Gln Pro Ile Lys Glu Ile Ser Gly Thr
1               5                  10                  15

Ile Lys Leu Pro Gly Ser Lys Ser Leu Ser Asn Arg Ile Leu Leu Leu
            20                  25                  30

Ala Ala Leu Ala Glu Gly Thr Thr Val Val Asp Asn Leu Leu Asp Ser
        35                  40                  45

Asp Asp Ile Arg Tyr Met Leu Ala Ala Leu Lys Thr Leu Gly Leu Thr
50                  55                  60

Val Glu Asp Asp Ser Val Met Lys Arg Ala Ser Val Val Gly Ser Gly
65                  70                  75                  80

Gly Gln Phe Pro Val Gly Lys Asp Ser Lys Glu Val Gln Leu Phe Leu
                85                  90                  95

Gly Asn Ala Gly Thr Ala Met Arg Pro Leu Thr Ala Ala Ile Ala
            100                 105                 110

Ala Gly Gly Asn Ala Ser Tyr Ile Leu Asp Gly Val Pro Arg Met Arg
        115                 120                 125

Glu Arg Pro Ile Gly Asp Leu Val Val Gly Leu Lys Gln Leu Gly Ala
130                 135                 140

Asp Val Asp Cys Ile Leu Gly Thr Asp Cys Pro Pro Val Arg Ala Asn
145                 150                 155                 160

Ala His Gly Gly Leu Pro Gly Gly Lys Val Lys Leu Ser Gly Ser Ile
            165                 170                 175

Ser Ser Gln Tyr Leu Thr Ala Leu Leu Met Ala Ala Pro Leu Ala Leu
        180                 185                 190

Gly Asp Val Glu Ile Glu Ile Met Asp Lys Leu Ile Ser Val Pro Tyr
            195                 200                 205

Val Glu Met Thr Leu Lys Leu Met Glu Arg Phe Gly Val Ser Val Glu
        210                 215                 220

His Ser Ser Ser Trp Asp Arg Phe Phe Ile Lys Gly Gly Gln Lys Tyr
225                 230                 235                 240

Lys Ser Pro Gly Asn Ala Tyr Val Glu Gly Asp Ala Ser Ser Ala Ser
                245                 250                 255

Tyr Phe Leu Ala Gly Ala Ala Val Thr Gly Gly Thr Val Thr Val Glu
            260                 265                 270
```

-continued

```
Gly Cys Gly Thr Ser Ser Leu Gln Gly Asp Val Arg Phe Ala Glu Val
        275                 280                 285

Leu Glu Lys Met Gly Ala Lys Val Thr Trp Thr Glu Asn Ser Val Thr
    290                 295                 300

Val Thr Gly Pro Pro Gln Asp Pro Ser Lys Lys Lys Arg Leu Arg Ala
305                 310                 315                 320

Val Asp Val Asn Met Asn Lys Met Pro Asp Val Ala Met Thr Leu Ala
                325                 330                 335

Val Val Ala Leu Tyr Ala Asp Gly Pro Thr Ala Ile Arg Asp Val Ala
            340                 345                 350

Ser Trp Arg Val Lys Glu Thr Glu Arg Met Ile Ala Ile Cys Thr Glu
        355                 360                 365

Leu Arg Lys Gln Gly Ala Thr Val Glu Glu Gly Pro Val Tyr Cys Val
    370                 375                 380

Ile Thr Pro Pro Glu Lys Leu Asn Ala Asn Ala Ile Asp Thr Tyr Asp
385                 390                 395                 400

Asp His Arg Met Ala Met Ala Phe Ser Leu Ala Ala Cys Ala Asp Val
                405                 410                 415

Pro Val Thr Ile Gly Asp Pro Gly Cys Thr Arg Lys Thr Phe Pro Asp
            420                 425                 430

Tyr Phe Glu Val Leu Gln Arg Phe Thr Thr His
        435                 440
```